US009976171B2

(12) United States Patent
Latino et al.

(10) Patent No.: US 9,976,171 B2
(45) Date of Patent: May 22, 2018

(54) METHOD FOR DISSOLUTION TESTING OF SOLID COMPOSITIONS CONTAINING DIGESTIVE ENZYMES

(75) Inventors: Massimo Latino, Cinisello Balsamo (IT); Luigi Ghidorsi, Milan (IT); Giovanni Ortenzi, Monza (IT)

(73) Assignee: ALLERGAN PHARMACEUTICALS INTERNATIONAL LIMITED (IE)

( * ) Notice: Subject to any disclaimer, the term of this patent is extended or adjusted under 35 U.S.C. 154(b) by 314 days.

(21) Appl. No.: 14/237,180

(22) PCT Filed: Aug. 8, 2012

(86) PCT No.: PCT/IB2012/054050
§ 371 (c)(1),
(2), (4) Date: Jun. 12, 2014

(87) PCT Pub. No.: WO2013/021359
PCT Pub. Date: Feb. 14, 2013

(65) Prior Publication Data
US 2014/0295474 A1    Oct. 2, 2014

Related U.S. Application Data

(60) Provisional application No. 61/521,227, filed on Aug. 8, 2011.

(51) Int. Cl.
| C12Q 1/44 | (2006.01) |
| G01N 33/573 | (2006.01) |
| G01N 33/15 | (2006.01) |
| G01N 21/64 | (2006.01) |

(52) U.S. Cl.
CPC ............. *C12Q 1/44* (2013.01); *G01N 33/573* (2013.01); *C12Q 2545/00* (2013.01); *G01N 33/15* (2013.01); *G01N 2021/6417* (2013.01)

(58) Field of Classification Search
CPC ................. G01N 33/573; G01N 33/15; G01N 2021/6417; C12Q 1/44; C12Q 2545/00
See application file for complete search history.

(56) References Cited

U.S. PATENT DOCUMENTS

| 3,844,891 A | 10/1974 | Hess et al. |
| 4,079,125 A | 3/1978 | Sipos |
| 4,237,229 A | 12/1980 | Hartdegen et al. |
| 4,280,971 A | 7/1981 | Wischniewski et al. |
| 4,447,412 A | 5/1984 | Bilton |
| 4,623,624 A | 11/1986 | Schultze |
| 4,704,295 A | 11/1987 | Porter et al. |
| 4,786,505 A | 11/1988 | Lovgren et al. |
| 4,849,227 A | 7/1989 | Cho |
| 4,859,471 A | 8/1989 | Fulberth et al. |
| 5,075,231 A | 12/1991 | Moreau et al. |
| 5,225,202 A | 7/1993 | Hodges et al. |
| 5,260,074 A | 11/1993 | Sipos |
| 5,306,506 A | 4/1994 | Zema et al. |
| 5,308,832 A | 5/1994 | Garleb et al. |
| 5,324,514 A | 6/1994 | Sipos |
| 5,378,462 A | 1/1995 | Boedecker et al. |
| 5,460,812 A | 10/1995 | Sipos |
| 5,570,104 A | 10/1996 | Hayashi |
| 5,578,304 A | 11/1996 | Sipos |
| 5,665,428 A | 9/1997 | Cha et al. |
| 5,733,575 A | 3/1998 | Mehra et al. |
| 5,733,763 A | 3/1998 | Markussen et al. |
| 5,750,104 A | 5/1998 | Sipos |
| 5,861,177 A | 1/1999 | Atzl et al. |
| 5,861,291 A | 1/1999 | Abboudi et al. |
| 6,051,220 A | 4/2000 | Scharpe |
| 6,313,102 B1 | 11/2001 | Colaco et al. |
| 6,318,650 B1 | 11/2001 | Breitenbach et al. |
| 6,352,974 B1 | 3/2002 | Ghirri et al. |
| 6,426,091 B1 | 7/2002 | Okumura et al. |
| 6,607,747 B2 | 8/2003 | Ullah et al. |
| 6,855,336 B2 | 2/2005 | Chen et al. |
| 6,955,903 B2 | 10/2005 | Kulkarni et al. |
| 7,201,923 B1 | 4/2007 | van Lengerich |
| 7,658,918 B1 | 2/2010 | Ortenzi et al. |
| 8,071,089 B2 | 12/2011 | Schuler et al. |
| 8,221,747 B2 | 7/2012 | Ortenzi et al. |
| 8,246,950 B2 | 8/2012 | Ortenzi et al. |

(Continued)

FOREIGN PATENT DOCUMENTS

| AU | 2011309763 B2 | 8/2015 |
| CA | 2263703 A1 | 8/1999 |

(Continued)

OTHER PUBLICATIONS

Sankalia M.G. et al., Papain Entrapment in Alginate Beads for Stability Improvement and Site-Specific Delivery: Physicochemical Characterization and Factorial Optimization Using Neural Network Modeling, AAPS PharmSciTech., 2005, vol. 6, No. 2, article 31, pp. E209-E222.*
Scheich C. et al., An automated in vitro protein folding screen applied to a human dynactin subunit, Protein Science, 2004, vol. 13, pp. 370-380.*
Miller D.A. et al., Evaluation of the USP dissolution test method A for enteric-coated articles by planar laser-induced fluorescence, International Journal of Phramaceuticals, 2007, vol. 330, pp. 61-72.*

(Continued)

*Primary Examiner* — Satyendra K Singh
(74) *Attorney, Agent, or Firm* — Carter, DeLuca, Farrell & Schmidt, LLP

(57) ABSTRACT

The invention is directed to a process for measuring the amount of digestive enzymes released from a solid composition in a dissolution medium by fluorescence spectroscopy. The invention is also directed to a combined method for measuring both the dissolution and gastroresistance of a solid compositions comprising pancrelipase.

20 Claims, 7 Drawing Sheets

(56) References Cited

U.S. PATENT DOCUMENTS

| | | | |
|---|---|---|---|
| 8,293,229 | B2 | 10/2012 | Ortenzi et al. |
| 8,562,978 | B2 | 10/2013 | Ortenzi et al. |
| 8,562,979 | B2 | 10/2013 | Ortenzi et al. |
| 8,562,980 | B2 | 10/2013 | Ortenzi et al. |
| 8,562,981 | B2 | 10/2013 | Ortenzi et al. |
| 8,784,884 | B2 | 7/2014 | Perrett et al. |
| 2001/0024660 | A1 | 9/2001 | Ullah et al. |
| 2001/0046493 | A1 | 11/2001 | Margolin et al. |
| 2002/0044965 | A1* | 4/2002 | Curatolo ............ A61K 9/0004 424/468 |
| 2002/0044968 | A1 | 4/2002 | van Lengerich |
| 2002/0054907 | A1 | 5/2002 | Devane et al. |
| 2002/0187536 | A1 | 12/2002 | Kulkarni et al. |
| 2004/0057944 | A1 | 3/2004 | Galle et al. |
| 2004/0101562 | A1 | 5/2004 | Maio |
| 2004/0121010 | A1 | 6/2004 | Hirsh et al. |
| 2004/0197321 | A1 | 10/2004 | Sipos et al. |
| 2004/0213847 | A1 | 10/2004 | Matharu et al. |
| 2005/0019417 | A1 | 1/2005 | Ko et al. |
| 2005/0158299 | A1 | 7/2005 | Margolin et al. |
| 2005/0208133 | A1 | 9/2005 | Tsutsumi et al. |
| 2005/0281876 | A1 | 12/2005 | Li et al. |
| 2006/0121017 | A1 | 6/2006 | Margolin et al. |
| 2006/0198838 | A1 | 9/2006 | Fallon |
| 2007/0025977 | A1 | 2/2007 | Mulberg |
| 2007/0141151 | A1 | 6/2007 | Silver et al. |
| 2007/0148151 | A1 | 6/2007 | Frink et al. |
| 2007/0148152 | A1 | 6/2007 | Shlieout et al. |
| 2007/0190142 | A1 | 8/2007 | Breitenbach et al. |
| 2008/0199448 | A1 | 8/2008 | Ross et al. |
| 2008/0274174 | A1 | 11/2008 | Ortenzi et al. |
| 2008/0279839 | A1 | 11/2008 | Schuler et al. |
| 2008/0279953 | A1 | 11/2008 | Ortenzi et al. |
| 2008/0299185 | A1 | 12/2008 | Ortenzi et al. |
| 2009/0081184 | A1 | 3/2009 | Margolin et al. |
| 2009/0117180 | A1 | 5/2009 | Ortenzi et al. |
| 2009/0148545 | A1 | 6/2009 | Falk et al. |
| 2009/0226414 | A1 | 9/2009 | Tijssen et al. |
| 2009/0232789 | A1 | 9/2009 | Fallon |
| 2010/0021537 | A1 | 1/2010 | Ortenzi et al. |
| 2010/0239559 | A1 | 9/2010 | Freedman et al. |
| 2010/0270183 | A1 | 10/2010 | Ortenzi et al. |
| 2011/0064799 | A1 | 3/2011 | Perrett et al. |
| 2011/0123605 | A1 | 5/2011 | Ortenzi et al. |
| 2011/0123633 | A1 | 5/2011 | Ortenzi et al. |
| 2011/0123634 | A1 | 5/2011 | Ortenzi et al. |
| 2012/0177629 | A1 | 7/2012 | Broussard et al. |
| 2012/0201875 | A1 | 8/2012 | Ortenzi et al. |
| 2013/0251926 | A1 | 9/2013 | Wood et al. |
| 2014/0170212 | A1 | 6/2014 | Ortenzi et al. |
| 2014/0287035 | A1 | 9/2014 | Perrett et al. |
| 2014/0295474 | A1 | 10/2014 | Latino et al. |

FOREIGN PATENT DOCUMENTS

| | | |
|---|---|---|
| CA | 2419572 A1 | 8/2004 |
| CN | 87103560 A | 5/1988 |
| CN | 1235824 A | 11/1999 |
| CN | 1376519 A | 10/2002 |
| CN | 1489476 A | 4/2004 |
| CN | 101430279 A | 5/2009 |
| CN | 103060296 A | 4/2013 |
| DE | 2730481 A1 | 1/1978 |
| DE | 19907764 A1 | 11/1999 |
| EA | 201290985 A1 | 5/2013 |
| EP | 8780 A2 | 3/1980 |
| EP | 0035780 A1 | 9/1981 |
| EP | 0115023 A2 | 8/1984 |
| EP | 0256127 A1 | 2/1988 |
| EP | 0283442 A1 | 9/1988 |
| EP | 304332 A2 | 2/1989 |
| EP | 0576938 A1 | 1/1994 |
| EP | 0879772 A2 | 11/1998 |
| EP | 1010423 A2 | 6/2000 |
| EP | 1279402 A1 | 1/2003 |
| EP | 1335706 B1 | 4/2005 |
| EP | 1579771 A1 | 9/2005 |
| EP | 1931316 A2 | 6/2008 |
| EP | 1967211 A1 | 9/2008 |
| EP | 2079445 A2 | 7/2009 |
| EP | 2477645 A4 | 7/2012 |
| EP | 2621476 A1 | 8/2013 |
| EP | 2621476 B1 | 7/2014 |
| EP | 2754437 A2 | 7/2014 |
| EP | 2818160 A1 | 12/2014 |
| ES | 489967 A1 | 10/1980 |
| FR | 2313916 A1 | 1/1977 |
| GB | 732951 A | 6/1955 |
| GB | 1509866 A | 5/1978 |
| GB | 2234973 A | 2/1991 |
| JP | S52-3819 A | 1/1977 |
| JP | 58-085159 | 5/1983 |
| JP | H05-38731 A | 2/1993 |
| JP | 538731 | 10/1993 |
| JP | H05-76928 B2 | 10/1993 |
| JP | 10-295374 A | 11/1998 |
| JP | H11-514088 A | 11/1999 |
| JP | 2002506527 A | 2/2002 |
| JP | 2004-513645 A | 5/2004 |
| JP | 4187085 B2 | 11/2008 |
| JP | 2010519217 A | 6/2010 |
| JP | 6043929 B2 | 12/2016 |
| KR | 20060127857 A | 12/2006 |
| KR | 100804096 B1 | 2/2008 |
| WO | 8705505 A1 | 9/1987 |
| WO | 90/09428 A1 | 8/1990 |
| WO | 9009440 A1 | 8/1990 |
| WO | 90/15856 A1 | 12/1990 |
| WO | 93/07859 A1 | 4/1993 |
| WO | 93/18753 A1 | 9/1993 |
| WO | 9325669 A1 | 12/1993 |
| WO | 9600773 A1 | 1/1996 |
| WO | 9746658 A1 | 12/1997 |
| WO | 98/01544 A1 | 1/1998 |
| WO | 97/46860 A3 | 2/1998 |
| WO | 98/58254 A1 | 12/1998 |
| WO | 01/25412 A1 | 4/2001 |
| WO | 01/70047 A1 | 9/2001 |
| WO | 0174980 A2 | 10/2001 |
| WO | 0240045 A2 | 5/2002 |
| WO | 02058735 A1 | 8/2002 |
| WO | 2004074470 A1 | 9/2004 |
| WO | 2005042012 A1 | 5/2005 |
| WO | 2005092370 A1 | 10/2005 |
| WO | 2006044529 A1 | 4/2006 |
| WO | 20060044529 A1 | 4/2006 |
| WO | 2007013752 A1 | 2/2007 |
| WO | 2007020259 A2 | 2/2007 |
| WO | 2007020260 A2 | 2/2007 |
| WO | 08/017659 A1 | 2/2008 |
| WO | 2008102264 A2 | 8/2008 |
| WO | 2009109856 A2 | 9/2009 |
| WO | 2011035079 A1 | 3/2011 |
| WO | 2011072069 A2 | 6/2011 |
| WO | 2011114224 A1 | 9/2011 |
| WO | 2012019186 A1 | 2/2012 |
| WO | 2012042372 A1 | 4/2012 |
| WO | 2012052853 A1 | 4/2012 |
| WO | 2013021359 A1 | 2/2013 |
| WO | 2014141121 A1 | 9/2014 |
| WO | 2015/019198 A2 | 2/2015 |
| WO | 2015/020943 A2 | 2/2015 |
| WO | 2015069677 A1 | 5/2015 |
| WO | 2015193730 A1 | 12/2015 |

OTHER PUBLICATIONS

Ramos P. et al., Time-Resolved Fluorescence Allows Selective Monitoring of Trp30 Environmental Changes in the Seven-Trp-Containing Human Pancreatic Lipase, Biochemistry, 2003, vol. 42, pp. 12488-12496.*

(56) References Cited

OTHER PUBLICATIONS

Russian Office Action (with English translation), dated Oct. 29, 2015, corresponding to Russian Application No. 2014104591; 7 total pages.
International Search Report, International Preliminary Report on Patentability and Written Opinion of the International Searching Authority, corresponding to International Application No. PCT/IB2012/054050, dated Nov. 14, 2012; 11 total pages.
A. Aloulou, et al., "In Vitro Comparative Study of Three Pancreatic Enzyme Preparations: Dissolution Profiles, Active Enzyme Release and Acid Stability", Alimentary Pharmacology & Therapeutics, vol. 27, No. 3; Oct. 29, 2007; pp. 283-292.
A. C. Mehta, "Review of analytical methods used in the dissolution testing of pharmaceuticals", Analytical Proceedings Including Analytical Communications, vol. 31, No. 8, Jan. 1, 1994; pp. 245-248.
Alexey Khrenov: "USP Pancrelipase update", Jul. 1, 2009 and Alexey Khrenov: "USP Enzyme Workshop: Pancrelipase Update", Jul. 1, 2009.
"Dissolution Toolkit—Procedures for Mechanical Calibration and Performance Verification Test", USP (U.S. Pharmacopeia), Mar. 22, 2010.
New Zealand First Examination Report corresponding to New Zealand Application No. 620329, dated Oct. 16, 2014; 2 pages.
Colombian Office Action (with English translation), dated Oct. 29, 2014, corresponding to Colombian Application No. 14-33910; 20 total pages including English translation.
Coutlee, et al., "Comparison of Colorimetric, Fluorescent, and Enzymatic Amplification Substrate Systems in an Enzyme Immunoassay for Detection of DNA-RNA Hybrids", Journal of Clinical Microbiology, vol. 27, No. 5, May 1989, pp. 1002-1007.
Fuhrmann, et al., "In Vivo Fluorescence Imaging of Exogenous Enzyme Activity in the Gastrointestinal Tract", Proceedings of the National Academy of Sciences of the USA, vol. 108, No. 22, May 2011; pp. 9032-9037.
Zhang, et al., "Quantitative Fluorescence Correlation Spectroscopy Reveals a 1000-Fold Increase in Lifetime of Protein Functionality", Biophysical Journal, vol. 95, Oct. 2008; pp. 3439-3446.
(Guidance for Industry) "SUPAC-MR: Modified Release Solid Oral Dosage Forms Scale-Up and Postapproval Changes: Chemistry, Manufacturing and Controls; In Vitro Dissolution Testing and In Vivo Bioequivalence Documentation" Center for Drug Evaluation and Research (CDER), Sep. 1997.
Australian Patent Examination Report No. 1, dated May 20, 2014, corresponding to Australian Application No. 2012293325; 3 pages.
Chinese Office Action (with No English translation), dated Dec. 2, 2014, corresponding to Chinese Application No. 201280040203.2; 6 pages.
International Search Report, Written Opinion and International Preliminary Report on Patentability based on International Application No. PCT/IB2008/000770, dated Jun. 3, 2009; 13 Pages.
Krishnamurty et al., "Delayed release pancrelipase for treatment of pancreatic exocrine insufficiency associated with chronic pancreatitis," Therapeutics and Clinical Risk Management, (2009:5) pp. 507-520.
Drugs@FDA Glossary of Terms, printed Nov. 20, 2009; http://www.fda.gov/Drugs/InformationonDrugs/ucm079436.htm; 7 pages.
Guidance for Industry #191, Changes to Approved NADAs—New NADAs vs. Category II Supplemental NADAs, Final Guidance, U.S. Department of Health and Human Services, Food and Drug Administration, Center for Veterinary Medicine, Released Nov. 19, 2009: 25 pages.
Singapore Written Opinion, corresponding to Singapore Patent Application No. 200905385-1, issued by the Austrian Patent Office dated Dec. 16, 2010; 6 pages.
Hageman, "The Role of Moisture in Protein Stability," Drug Development and Industrial Pharmacy, vol. 14, No. 14, (1988); pp. 2047-2070.
Maul and Schmidt, "Influence of different-shaped pigments on bisacodyl release from Eudragit L 30 D," International Journal of Pharmacetuics, vol. 118, No. 1, May 1, 1995; pp. 103-112.
Parker et al., "Effects of Solids-Loading on Moisture Permeability Coefficients of Free Films," Journal of Pharmaceutical Sciences, vol. 63, No. 1 (Jan. 1974); pp. 119-125.
Thoma and Bechtold, "Influence of aqueous coatings on the stability of enteric coated pellets and tablets," European Journal of Pharmaceutics and Biopharmaceutics, vol. 47, (1999), pp. 39-50.
Australian First Examination Report, dated Mar. 23, 2012, corresponding to Australian Patent Application No. 2008218595; 2 pages.
English Translation of Second Chinese Office Action, dated Apr. 12, 2012, corresponding to Chinese Patent Application No. 200880012762.6; 5 pages.
European Communication, dated Jan. 3, 2012, corresponding to European Patent Application No. 08719392.6; 7 pages.
European Communication, dated Aug. 1, 2012, corresponding to European Patent Application No. 08719392.6; 7 pages.
New Zealand First Examination Report, dated Aug. 26, 2010, corresponding to New Zealand Patent Application No. 579047; 3 pages.
New Zealand Second Examination Report, dated Dec. 15, 2011, corresponding to New Zealand Patent Application No. 579047; 2 pages.
New Zealand First Examination Report, dated Feb. 29, 2012, corresponding to New Zealand Patent Application No. 598477; 1 page.
Singapore Second Written Opinion, dated Nov. 22, 2011, corresponding to Singapore Patent Application No. 200905385-1; 6 pages.
U.S. Office Action, dated Mar. 20, 2012, corresponding to U.S. Appl. No. 12/034,480; 7 pages.
U.S. Office Action, dated Oct. 14, 2011, corresponding to U.S. Appl. No. 12/034,480; 15 pages.
U.S. Office Action, dated Mar. 19, 2012, corresponding to U.S. Appl. No. 12/034,488; 8 pages.
U.S. Office Action, dated Oct. 25, 2011, corresponding to U.S. Appl. No. 12/034,488; 14 pages.
U.S. Office Action, dated Jan. 4, 2012, corresponding to U.S. Appl. No. 12/034,491; 7 pages.
U.S. Office Action, dated Jun. 23, 2011, corresponding to U.S. Appl. No. 12/034,491; 7 pages.
U.S. Office Action, dated Jun. 26, 2012, corresponding to U.S. Appl. No. 13/019,844; 15 pages.
U.S. Office Action, dated May 24, 2012, corresponding to U.S. Appl. No. 13/019,856; 9 pages.
U.S. Office Action, dated May 23, 2012, corresponding to U.S. Appl. No. 13/019,860; 5 pages.
U.S. Office Action, dated Jul. 2, 2012, corresponding to U.S. Appl. No. 12/832,596; 11 pages.
International Search Report and Written Opinion, dated Oct. 22, 2012, corresponding to International Application No. PCT/US2010/049203; 6 pages.
Canadian Office Action, dated May 6, 2014, corresponding to Canadian Application No. 2,677,989, 2 pages.
Colombian Office Action (with No English translation), dated May 26, 2014, corresponding to Colombian Application No. 09.101.677; 4 pages.
Costa Rica Preliminary Technical Report—1st Phase (with English Translation), dated Jun. 12, 2014, corresponding to Costa Rican Application No. 11031; 11 total pages.
European Communication, dated Apr. 8, 2014, corresponding to European Patent Application No. 08719392.6; 6 pages.
English Translation of Indian First Examination Report, dated Oct. 17, 2014, corresponding to Indian Application No. 5854/DELNP/2009; 4 pages.
Singapore Search Report, dated Apr. 7, 2014 and Singapore Written Opinion, dated Apr. 28, 2014, corresponding to Singapore Application No. 2012091583; 11 total pages.

(56) References Cited

OTHER PUBLICATIONS

Japanese Decision of Rejection and Decision of Dismissal of Amendment (with English Translations), dated Aug. 25, 2014, corresponding to Japanese Application No. 2009-549868; 9 total pages.
Japanese Notice of Reasons for Rejection (with English translation), dated Jan. 19, 2015, corresponding to Japanese Application No. 2013-265143, 7 total pages.
Taiwanese Search Report (with English translation) and Taiwanese Office Action (with No English translation), dated Oct. 3, 2014, corresponding to Taiwanese Application No. 102138934; 10 total pages.
Colombian Office Action (with No English translation), dated Sep. 23, 2014, corresponding to Colombian Application No. 14.026.502, 4 pages.
The Decision of the Enlarged Board of Appeal, dated Nov. 22, 2013, 18 pages.
The Minutes of the Oral Proceedings of Nov. 22, 2013, 6 pages.
Communication from the Enlarged Board of Appeal pursuant to Articles 13 and 14(2) RPEBA, corresponding to Case No. R 06/13, dated Sep. 17, 2013; 6 pages.
Letter from Botti & Ferrari regarding a Petition for Review of Decision T0977/09-3.3.02, European Patent No. 1 335 706 in the name of Aptalis Pharma S.r.l., dated May 15, 2013; 12 pages.
Termination of Opposition Proceedings of Patent No. 01994654.0-1456 / 1335706 with Revocation of the Patent, dated Mar. 14, 2013; 2 pages.
Decision, dated Nov. 30, 2012, corresponding to Appeal No. T0977/09-3.3.02; 28 pages.
The Minutes of the Oral Proceedings of Nov. 30, 2012, corresponding to Appeal No. T0977/09-3.3.02; 18 pages.
A. Aloulou, et al., "In Vitro Comparative Study of Three Pancreatic Enzyme Preparations: Dissolution Profiles, Active Enzyme Release and Acid Stability," Alimentary Pharmacology & Therapeutics, vol. 27, No. 3; Oct. 29, 2007; pp. 283-292.
Final Office Action issued by the U.S. Patent and Trademark Office dated Jul. 14, 2008, corresponding to U.S. Appl. No. 10/416,702, 12 pages.
Fuhrmann, Vorlesungen uber, Technische Mykologie, Verlag Gustav Fisher 1913, 80; (D19); 4 pages.
Mesh to Micron Conversion Chart—Fluideng.com, Copyright 2002—Property of TM Industrial Supply, Inc.; (D20); http://www.fluideng.com/FE/meshmicron.html; 1 page.
Summary of facts and submissions, Grounds for the Decision (ANNEX)—opposition, corresponding to Application No. 01 994 654.0, dated Feb. 23, 2009; 9 pages.
Interlocutory Decision in Opposition proceedings, corresponding to Application No. 01 994 654.0-2107, dated Feb. 23, 2009; 2 pages.
Provision of the minutes in accordance with Rule 124(4) EPC, dated Feb. 23, 2009, corresponding to Application No. 01 994 654.0-2107; 12 pages.
Non-patent literature, dated Jul. 30, 2012, relating to the Appeal Procedure, (Eisenfuhr Speiser); 7 pages.
Letter from Botti & Ferrari, dated Jun. 27, 2012, relating to the Appeal Procedure, 10 pages.
Non-patent literature cited during the Appeal Procedure, (Eisenfuhr Speiser), Grounds of Appeal, dated Jun. 30, 2009; 24 pages.
Letter from Botti & Ferrari, dated Sep. 18, 2009, relating to the Appeal Procedure, 15 pages.
Royce, et al., Alternative Granulation Technique: Melt Granulation, Drug Development and Industrial Pharmacy, (D4) 22(9&10), 917-924; Copyright 1996 by Marcel Dakker, Inc.
Notice of Opposition to a European Patent and opposition documents related to Patent No. EP 1 335 706 B1, (Opposition file history as of Jan. 14, 2009, excluding non-duplicative, non-administrative documents; (92 total pages).
Non-patent literature dated Sep. 30, 2011, relating to the Appeal Procedure, (Eisenfuhr Speiser); 2 pages.
Non-patent literature cited during the Appeal Procedure, (universitatbonn) (D23), dated Sep. 20, 2011; 15 pages.

Sincero, et al., "Detection of hepatitis A virus (HAV) in oysters (*Crassostrea gigas*)," Water Research, Elsevier, Amsterdam, NL, vol. 40, No. 5, Mar. 1, 2006; pp. 895-902.
Langeveld, et al, "Inactivated recombinant plant virus protects dogs from a lethal challenge with canine parvovirus," Vaccine, Elsevier, vol. 19, No. 27, Jun. 14, 2001, pp. 3661-3670.
Singh, et al., "Canine parvovirus-like particles, a novel nanomaterial for tumor targeting," Journal of Nanobiotechnology 2006, vol. 4, No. 2, dated Feb. 13, 2006; 11 pages.
Shieh, et al., "A method to detect low levels of enteric virus in contaminated oysters", Applied and environmental Microbiology, vol. 65, No. 11, Nov. 1999; pp. 4709-4714.
Bergeron, et al., Genomic Organization and Mapping of Transcription and Translation Products of the NADL-2 Strain of Porcine Parvovirus, Virology, 1993, 197(1): pp. 86-98.
Bergeron, J., Hebert, B. and Tijssen, P., Genomic Organization of the Kresse Strain of Porcine Parvovirus: Identification of the Allotropic Determinant and Comprison with Those of NADL-2 and Field Isolates, Journal of Virology vol. 70, No. 4, Apr. 1996; pp. 2508-2515.
Simpson, et al., "The Structure of Porcine Parvovirus: Comparison With Related Viruses," J. Mol. Biol., 2002, 315(5); pp. 1189-1198.
Szelei, et al., "Porcine Parvovirus". In: Kerr, et al., eds, Parvoviruses, London: Hodder Arnold; 2006; pp. 434-445.
Canaan, et al., "Interfacial Enzymology of Parvovirus Phospholipases A2," Journal of Biologizal Chemistry vol. 279, No. 15, Apr. 9, 2004; pp. 14502-14508.
Zadori, et al., 2001, "A Viral Phospholipase A2 is Required for Parvovirus Infectivity," Developmental Cell, vol. 1, Aug. 2001; pp. 291-302.
Zadori, et al., "SAT: a Late NS Protein of Porcine Parvovirus," Journal of Virology, vol. 79, No. 20; Oct. 2005; pp. 13129-13138.
Mullendore, et al., Improved Method for the Recovery of Hepatitis A virus from oysters, Journal of Virological Methods 94, pp. 25-35 (2001).
Sair, et al., "Improved Detection of Human Enteric Viruses in Foods by RT-PCR", Journal of Virological Methods 100, pp. 57-69 (2002).
Guevremont, et al., "Development of an Extraction and Concentration Procedure and Comparison of RT-PCR Primer Systems for the Detection of Hepatitis A Virus and Norovirus GII in Green Onions", Journal of Virological Methods 134; pp. 130-135 (2006).
Termination of Opposition Proceedings of Patent No. 01994654.0-1456 / 1335706 with Revocation of the Patent, dated May 14, 2014; 2 pages.
International Search Report, dated Jun. 23, 2014, corresponding to International Application No. PCT/IB2014/059722; 4 pages.
Ferrie, et al., "Pancreatic Enzyme Supplementation for Patients Receiving Enteral Feeds," Techniques and Procedures, Nutrition in Clinical Practice, vol. 26, No. 3, Jun. 2011; pp. 349-351.
Chen, et al., "Enteral Nutrition Formulas: Which Formula is Right for your Adult Patient," Invited Review, Nutrition in Clinical Practice, vol. 24, No. 3, Jun./Jul. 2009; pp. 344-355.
Alexey Khrenov: "USP Pancrelipase Update," dated Jul. 1, 2009, and Alexey Khrenov: "USP Enzyme Workshop: Pancrelipase Update," dated Jul. 1, 2009; 12 total pages.
"Dissolution Toolkit—Procedures for Mechanical Calibration and Performance Verification Test," USP (U.S, Pharmacopeia), dated Mar. 22, 2010; 16 pages.
New Zealand First Examination Report, dated Oct. 16, 2014, corresponding to New Zealand Application No. 620329; 2 pages.
Colombian Office Action (with English Translation), dated Oct. 29, 2014, corresponding to Colombian Application No. 14-33910; 20 total pages.
Coutlee, et al., "Comparison of Colorimetric, Fluorescent, and Enzymatic Amplification Substrate Systems in an Enzyme Immunoassay for Detection of DNA-RNA Hybrids," Journal of Clinical Microbiology, vol. 27, No. 5, May 1989; pp. 1002-1007.
Fuhrmann, et al., "In Vivo Fluorescence Imaging of Exogenous Enzyme Activity in the Gastrointestinal Tract," Proceedings of the National Academy of Sciences of the USA, vol. 108, No. 22, May 2011; pp. 9032-9037.

(56) References Cited

OTHER PUBLICATIONS

Zhang, et al., "Quantitative Fluorescence Correlation Spectroscopy Reveals a 1000-Fold Increase in Lifetime of Protein Functionality," Biophysical Journal, vol. 95, Oct. 2008; pp. 3439-3446.
(Guidance for Industry) "SUPAC-MR: Modified Release Solid Oral Dosage Forms—Scale-Up and Postapproval Changes: Chemistry, Manufacturing and Controls; In Vitro Dissolution Testing and In Vivo Bioequivalence Documentation" Center for Drug Evaluation and Research (CDER), Sep. 1997; 52 pages.
Eurasian Office Action (with English Translation), dated Jun. 30, 2014, corresponding to Eurasian Application No. 201390409; 5 total pages.
Australian Patent Examination Report No. 1, dated Oct. 14, 2014, corresponding to Australian Application No. 2011309763; 3 pages.
European Search Report, dated Nov. 28, 2014, corresponding to European Application No. 14176579.2; 4 pages.
Chinese Office Action (With No English translation), dated Jan. 6, 2015, corresponding to Chinese Application No. 201180055719.X; 18 pages.
Masaki Hasegawa, Direct Compression "Microcrystalline Cellulose Grade 12 versus Classic Grade 102," Pharmaceutical Technology, May 2002; pp. 50-60.
Australian Patent Examination Report No. 1, dated Apr. 28, 2014, corresponding to Australian Application No. 2010295494; 3 pages.
Extended European Search Report, dated May 26, 2014, corresponding to European Application No. 10817867.4; 6 pages.
Symersky T., et al. "An Explorative Study on the Effect of Enzyme Supplementation in Patients Recovered From Acute Pancreatitis," Gastroenterology 2004; 126 (4 suppl 2): A85, Abstract 653.
Taiwanese Office Action (with No English translation), dated Jul. 21, 2014, corresponding to Taiwanese Application No. 099131496; 6 pages.
Taiwanese Search Report (with No English translation, dated Jul. 16, 2014, corresponding to Taiwanese Application No. 099131496; 1 page.
Russian Office Action (with English Translation), dated Jul. 7, 2014, corresponding to Russian Application No. 2012113253; 8 total pages.
Colombian Office Action (with No English Translation), dated Aug. 22, 2014, corresponding to Colombian Application No. 12-50658; 9 pages.
Chilean Office Action (with No English Translation), dated Oct. 8, 2014, corresponding to Chilean Patent Application No. 00658-2012; 8 pages.
Japanese Notice of Rejection (with English Summary Translation), dated Sep. 24, 2014, corresponding to Japanese Application No. 2012-529909; 6 pages.
Chinese Office Action (with No English translation), dated Nov. 24, 2014, corresponding to Chinese Application No. 201080041366.3; 3 pages.
Russian Office Action (with English translation), dated Nov. 25, 2014, corresponding to Russian Application No. 2012113253; 11 total pages.
Taiwanese Office Action (with English translation), dated Nov. 26, 2014, corresponding to Taiwanese Application No. 099131496; 10 total pages.
English translation of Israeli Office Action, dated Nov. 23, 2014, corresponding to Israeli Application No. 218656; 2 pages.
Eurasian Office Action (with English Translation), dated Jan. 30, 2015, corresponding to Eurasian Applicaion No. 201390409/28; 4 total pages.
Avicel-FMC, Avicel product sheet, Apr. 22, 2010.
International Search Report, and Written Opinion of the International Searching Authority, corresponding to International Application No. PCT/IB2011/002419, dated Feb. 6, 2012; 8 total pages.
Korean Office Action (with English translation), dated Nov. 24, 2014, corresponding to Korean Application No. 10-2009-7019590; 6 total pages.
Non-patent literature cited during the Appeal Procedure (universitatbonn) (D22), dated Jun. 17, 2010; 6 pages.
Non-patent literature relating to the Appeal Procedure, dated Aug. 5, 2010, (Eisenfuhr Speiser); 10 pages.
Letter from Prof. Dr. Klaus-Jurgen Steffens, Rheinische Friedrich-Wilhelms-Universitat Bonn to the European Patent Office, Munich, dated Jun. 17, 2010, "Expert Opinion for Presentation at the European Patent Office"; 6 pages.
ScienceLab.com, Chemicals & Laboratory Equipment, Polyethylene Glycol 400 MSDS, Material Safety Data Sheet (D12), dated Oct. 10, 2005; 6 pages.
Caelo, Macrogol 4000 Pulver, Sicherheitsdatenblatt, Seite1, von 3, (D15), dated Aug. 4, 2008; 3 pages.
Office Action issued by the U.S. Patent and Trademark Office dated Apr. 1, 2009, corresponding to U.S. Appl. No. 10/416,702, 24 pages.
US Pharmacopeia, Chapter 786, Particle Size Distribution Estimation by Analytical Sieving, Web download, Jun. 26, 2009; 5 pages.
Gohel, "A Review of Co-Processed Directly Compressible Excipients," J. Pharm. Pharmaceutical Sciences, 8(1); pp. 76-93; (2005).
Non-patent literature cited during the Appeal Procedure, Eisenfuhr Speiser, Feature Analysis, dated Aug. 5, 2010; 1 page.
International Search Report and Written Opinion of the International Searching Authority, dated Mar. 13, 2015, corresponding to International Application No. PCT/US14/63984; 9 total pages.
Canadian Office Action dated Mar. 18, 2015 and Canadian Examination Search Report dated Mar. 10, 2015, corresponding to Canadian Application No. 2,677,989; 4 total pages.
International Search Report and Written Opinion of the International Searching Authority, dated Mar. 2, 2015, corresponding to International Application No. PCT/IB2014/002583; 13 total pages.
Hwang, et al., "Selective Precipitation of Proteins From Pancreatin Using Designed Antisolvents", Industrial & Engineering Chemistry Research, vol. 46, No. 12, Jun. 1, 2007; pp. 4289-4294.
International Search Report, and Written Opinion of the International Searching Authority, corresponding to International Application No. PCT/US14/49569, dated Nov. 14, 2014; 8 total pages.
Queensland Government, "Tube Feeding at Home," Jan. 15, 2011, http://www.ausee.org/tube%20Feeding.pdf; 27 pages (Especially p. 13, Paragraph 3).
Wohlt, et al., "Recommendations for the Use of Medications with Continuous Enteral Nutrition," Am J Health Syst Pharm., 2009, 15 pages (Especially p. 4, Paragrah 7 and p. 5, Paragraph 1).
Singapore Search and Examination Report, dated Jan. 8, 2015, corresponding to Singapore Application No. 2012091583; 6 pages.
European Communication, dated Jan. 8, 2015, corresponding to European Patent Application No. 14176579.2; 2 pages.
International Search Report and Written Opinion of the International Searching Authority, corresponding to International Application No. PCT/US14/63984, dated Mar. 13, 2015; 10 total pages.
Chinese First Office Action and Search Report (English translations), dated Apr. 3, 2015, corresponding to Chinese Patent Application No. 201410059861.7; 23 total pages.
Israeli Office Action dated May 10, 2015 (No English translation), corresponding to Israeli Patent Application No. 200407; 2 pages.
European extended Search Report, dated Jun. 2, 2015, corresponding to European Patent Application No. 14150794.7; 10 pages.
Japanese Office Action (No English translation), dated May 12, 2015, corresponding to Japanese Patent Application No. 2013-530811; 3 pages.
Russian Office Action (with English translation), dated Jun. 15, 2015, corresponding to Russian Patent Appplication No. 2014104591/15; 10 total pages.
Colombian Office Action (No English Translation Available), dated Sep. 30, 2015, corresponding to Colombian Application No. 14-33910; 11 pages.
International Preliminary Report on Patentability and Written Opinion of the International Searching Authoirty, corresponding to International Application No. PCT/IB2014/059722, dated Sep. 15, 2015; 9 Pages.
Canadian Office Action dated Jul. 3, 2015, corresponding to Canadian Patent Application No. 2,774,269; 4 pages.
English translation of Japanese Final Office Action, dated Jul. 7, 2015, corresponding to Japanese Patent Application No. 2012-529909; 2 pages.

(56) References Cited

OTHER PUBLICATIONS

Chilean Office Action (No English Translation Available), dated Jul. 22, 2015, corresponding to Chilean Patent Application No. 00658-2012; 8 pages.
Australian Patent Examination Report 1, dated Sep. 15, 2015, corresponding to Australian Patent Application No. 2014253526; 3 pages.
Communication of a Notice of Opposition to a European Patent Application and opposition documents related to Patent Application No. EP 117885223.3, dated Aug. 5, 2015 (678 total pages) (This Document Has Been Split Into Two Attachments in Order to Upload to EFSWEB, i.e., pp. 1-350 and pp. 351-678).
U.S. Appl. No. 61/389,037, filed Oct. 1, 2010 (prosecution history).
Chinese Office Action (No English translation available), dated Jul. 28, 2015, corresponding to Chinese Patent Application No. 201180055719.X; 13 pages.
Eurasian Search Report (with English translation) issued by the Eurasian Patent Organization (EAPO) dated Sep. 16, 2015, corresponding to Eurasian Patent Application No. 201590836; 4 total pages.
Eurasian Search Report (with English translation) issued by the Eurasian Patent Organization (EAPO) dated Sep. 16, 2015, corresponding to Eurasian Patent Application No. 201590835; 4 total pages.
Ukrainian Office Action (with English Translation) dated Sep. 23, 2015, corresponding to Ukraine Application No. a 2013 03847; 11 total pages.
European Communication dated Jul. 6, 2015, corresponding to European patent application No. 14150794.7; 2 pages.
Korean Notice of Preliminary Rejection (with English translation), dated Jun. 12, 2015, corresponding to Korean patent application No. 10-2015-7004820; 16 total pages.
Australian Patent Examination Report No. 1, dated Jul. 6, 2015, corresponding to Australian Patent Application No. 2014203364; 4 pages.
Canadian Office Action and Examination Search Report dated Sep. 3, 2015, corresponding to Canadian Patent Application No. 2,677,989; 4 total pages.
Japanese Decision of Rejection (with English translation) dated Sep. 25, 2015, corresponding to Japanese Application No. 2013-265143; 9 total pages.
Opposition filed in EP 2621476 dated Aug. 5, 2015, 22 pages.
English translation of Chinese Second Office Action dated Dec. 21, 2015, corresponding to Chinese Application No. 201410059861.7; 5 pages.
Taiwanese Office Action (with English translation), dated Nov. 3, 2015, corresponding to Taiwanese Application No. 102138934; 16 total pages.
Japanese Office Action (with English translation), dated May 12, 2015, corresponding to Japanese Patent Application No. 2013-530811; 8 total pages.
International Search Report and Written Opinion of the International Searching Authority dated Nov. 20, 2015, corresponding to International Application No. PCT/IB2015/001237; 17 total pages.
Schielke et al., "Thermal Stability of Hepatitis E. Virus Assessed by a Molecular Biological Approach," Virology Journal, Biomed Central, vol. 8, No. 1, Oct. 31, 2011; 9 pages.
Eurasian Office Action (With English Translation) dated Oct. 30, 2015, correpsonding to Eurasian Application No. 201390409/28; 4 total pages.
English translation of Israeli Office Action dated Jan. 11, 2016, corresponding to Israeli Patent Application No. 225504; 3 pages.
International Written Opinion of the International Searching Authority and International Search Report dated Jan. 19, 2010, corresponding to International Application No. PCT/IB2009/000472; 7 total pages.
International Preliminary Report on Patentability and Written Opinion of the International Searching Authority, dated Jan. 26, 2016, corresponding to International Application No. PCT/IB2014/002583; 10 total pages.

Communication of the Board of Appeal, corresponding to Appeal No. T2255/12-3.3.07, dated Mar. 7, 2016; 11 pages.
Non-Patent Literature document—"Oppoistion against European Patent No. 1 931 316 in the anme of Abbott Products GmbH," correspnding to Appeal No. T2255/12-3.3.07, (letter from Botti & Ferrari, to the European Patent Office), dated May 13, 2013; 9 pages.
Non-Patent Literature document—"Notice of Appeal against the decision revoking the patent further to opposition proceedings," (from Cabinet Beau de Lomenie to the European Patent Office), corresponding to European Patent No. 1 931 316, dated Oct. 26, 2012; 1 page.
Non-Patent Literature document—"Grounds of Appeal", (from Cabinet Beau de Lomenie to the European Patent Office), corresponding to European Patent No. 1 931 316, dated Jan. 2, 2013; 10 pages.
Non-Patent Literature document—"Decision revoking the European Patent," issued by the European Patent Office, corresponding to European Patent No. 1 931 316, dated Sep. 5, 2012; 14 pages.
Non-Patent Literature document—"Persons attending oral proceedings on patentee's side," (from Cabinet Beau de Lomenie to the European Patent Office), corresponding to European Patent No. 1 931 316, dated May 2, 2012; 1 page.
Non-Patent Literature document—"Submission in opposition proceedings," issued by the European Patent Office, corresponding to European Patent No. 1 931 316, dated May 2, 2012; 1 page.
Non-Patent Literature document—"Reply to summons to attend oral proceedings; filing of new main claim request," (from Cabinet Beau de Lomenie to the European Patent Office), corresponding to European Patent No. 1 931 316, dated Feb. 23, 2012; 2 pages.
Non-Patent Literature document—"Submission in opposition proceedings," issued by the European Patent Office, corresponding to European Patent No. 1 931 316, dated Feb. 23, 2012; 2 pages.
Non-Patent Literature document—Letter from Europatent to European Patent Office, corresponding to European Patent No. 1 931 316, dated Feb. 6, 2012; 1 page.
Thoma et al., "Influence of aqueous coatings on the stability of enteric coated pellets and tablets," European Journal of Pharmaceutics and Biopharmaceutics, Elsevier, (D11), vol. 47(1), (1999); pp. 39-50.
Non-Patent Literature document—"Submission in opposition proceedings," issued by the European Patent Office, corresponding to European Patent No. 1 931 316, dated Jan. 11, 2012; 2 pages.
Non-Patent Literature document—"Inquiry concerning summons to oral proceedings," (from Cabinet Beau de Lomenie to the European Patent Office), corresponding to European Patent No. 1 931 316, dated Jan. 11, 2012; 1 page.
Non-Patent Literature document—"Brief Communication, Communication pursuant to Article 1(2) of the decision of the President of the EPO dated Jul. 12, 2007 concerning the filing of authorisations and Communication of amended entries concerning the representative," dated Sep. 20, 2011, issued by the European Patent Office, corresponding to European Patent No. 1 931 316; 3 total pages.
Non-Patent Literature document—"Notice of Opposition Filed by Eurand S.p.A.," (from Abbott Products GmbH), corresponding to European Patent No. 1 931 316, dated Jun. 7, 2011; 6 pages.
Non-Patent Literature document—"Notice of Opposition against the European Patent EP-B-1 931 316", (letter from Botti & Ferrari to the European Patent Office), dated Nov. 15, 2010, 12 pages.
Malaysian Office Action dated Mar. 31, 2016, corresponding to Malaysian Application No. PI 2012001215; 3 pages.
Non-Patent Literature document—"Brief Communication," dated Feb. 10, 2011, issued by the European Patent Office, corresponding to European Application No. 06778240.9 (European Patent No. 1 931 316); 1 page.
Non-Patent Literature document—"Vollmacht Authorisation Pouvoir," (German document—Power of Representation before the EPO for European Patent No. 1 931 316, dated Sep. 13, 2011; 3 total pages.
Non-Patent Literature document—"Claims—First Auxiliary Request" and "Claims—Second Auxiliary Request," dated Sep. 2011, corresponding to Opposition Proceedings of European Patent No. 1 931 316; 12 total pages.

(56) References Cited

OTHER PUBLICATIONS

Non-Patent Literature document—"Brief Communication—Main Request,", dated Jun. 17, 2011, corresponding to European Patent No. 1 931 316; 8 total pages.
Non-Patent Literature document—"Notice of Opposition to a European Patent," dated Nov. 15, 2010, corresponding to European Patent No. 1 931 316; 5 pages.
Non-Patent Literature document—"Decision to grant a European patent pursuant to Article 97(1) EPC," corresponding to European Patent No. 1 931 316; dated Jan. 21, 2010; 2 pages.
Non-Patent Literature document—"A2PAMPHLET," related to WO 2007/020259 (PCT/EP2006/065311), printed on May 19, 2008; 29 total pages.
Non-Patent Literature document—"Claims (EP 06 778 240)," printed Sep. 25, 2008; 12 total pages.
Naftifine HCI—MSDS—Material Safety Data Sheet, created Jun. 23, 2004; http://pharmacycode.com/msds/Naftifine_HCI; 4 pages.
Australian Patent Examination Report No. 2, dated Feb. 25, 2016, corresponding to Australian Application No. 2014203364; 5 pages.
Egyptian Office Action (No English translation available), dated Mar. 20, 2016, corresponding to Egyptian Application No. PCT 1257/2009; 5 pages.
Chinese Office Action (No English translation available), dated Feb. 15, 2016, corresponding to Chinese Application No. 201180055719.X; 14 pages.
Mexican Office Action (No English translation available), corresponding to Mexican Application No. MX/a/2013/003627, dated Mar. 10, 2016; 2 pages.
International Preliminary Report on Patentability and Written Opinion of the International Searching Authority, dated Feb. 9, 2016, corresponding to International Application No. PCT/US2014/049569; 7 total pages.
Korean Notice of Final Rejection (with English translation), dated Dec. 28, 2015, corresponding to Korean Application No. 10-2015-7004820; 8 total pages.
Canadian Office Action dated Mar. 16, 2016, corresponding to Canadian Application No. 2,677,989; 4 pages.
Israeli Office Action (No English translation available), dated Apr. 3, 2016, corresponding to Israeli Application No. 218656; 2 pages.
Sankalia M.G. et al., "Papain Entrapment in Alginate Beads for Stability Improvement and Site-Specific Delivery: Physicochemical Characterization and Factorial Optimization Using Neural Network Modeling," AAPS PharmSciTech., 2005; vol. 6, No. 2, Article 31; pp. E209-E222.
Scheich C. et al., "An Automated In Vitro Protein Folding Screen Applied to a Human Dynactin Subunit," Protein Science, 2004, vol. 13; pp. 370-380.
Miller D.A. et al., "Evaluation of the USP Dissolution Test Method A for Enteric-Coated Articles by Planar Laser-Induced Fluorescence," International Journal of Pharmaceuticals, 2007, vol. 330; pp. 61-72.
Ramos et al., "Time-Resolved Fluorescence Allows Selective Monitoring of Trp30 Environmental Changes in the Seven-Trp-Containing Human Pancreatic Lipase," Biochemistry 2003, vol. 42; pp. 12488-12496.
Colombian Office Action (No English translation available), dated Feb. 19, 2016, corresponding to Colombian Application No. 14-026502; 8 pages.
Taiwanese Office Action with English tranlsation of Search Report, dated May 13, 2016, corresponding to Taiwaense Application No. 099131496; 5 total pages.
Eurasian Office Action (with English translation), dated May 30, 2016, corresponding to Eurasian Application No. 201590835/28; 4 total pages.
Eurasian Office Action (with English translation), dated May 30, 2016, corresponding to Eurasian Application No. 201590836/28; 4 total pages.
Eurasian Office Action (with English translation), dated Jun. 8, 2016, corresponding to Eurasian Application No. 201390409/28; 4 total pages.
Chinese Office Action (No English language translation available), dated Jul. 5, 2016, corresponding to Japanese Application No. 201180055719.X; 14 pages.
Australian Patent Examination Report No. 3, dated Jun. 28, 2016, corresponding to Australian Application No. 2014203364; 3 pages.
English translation of Chinese Third Office Action, dated Jun. 28, 2016, corresponding to Chinese Application No. 201410059861.7; 4 pages.
Korean Office Action (with English translation) dated May 16, 2016, corresponding to Korean Application No. 10-2015-7004820; 10 total pages.
Worthington Biochemical Corporation, Lipase—Worthington Enzyme Manual, Triacylglycerol acylhydrolase, (D14); www.worthington-biochem.com; Jun. 24, 2009; 2 pages.
Answers.com, Stir: Difinition, Synonyms of the word "Stir" from Answers.com, (D16), Jun. 24, 2009; 9 pages.
Chilean Office Action (No English translation available), dated Aug. 22, 2016, corresponding to Chilean Patent Application No. 2014-00315; 8 pages.
European Search Report dated Jan. 22, 2016, corresponding to European Application No. 15178147.3; 9 pages.
Japanese Office Action (No English translation available), dated Mar. 1, 2016, corresponding to Japanese Application No. 2014-524476; 3 total pages.
Australian Patent Examination Report No. 1, dated Sep. 21, 2016, corresponding to Australian Application No. 2015243026; 3 pages.
English translation of Israeli Office Action dated Aug. 30, 2016, corresponding to Israeli Application No. 243627; 2 pages.
Takanami et al., "Enzyme-assisted Purification of Two Phloem-limited Plant Viruses: Tobacco Necrotic Dwarf and Potato Leafroll", J. gen. Virol., vol. 44, (1979); pp. 153-159.
Tolin et al., "Purification and Serology of Peanut Mottle Virus", The American Phytopathological Society, vol. 73, No. 6, 1983; pp. 899-903.
Casas et al., "Detection of enterovirus and hepatitis A virus RNA in mussels (*Mytilus* spp.) by reverse transcriptase-polymerase chain reaction", Journal of Applied Microbiology, vol. 90, 2001; pp. 89-95.
Lewis et al., "Polyethylene Glycol Precipitation for Recovery of Pathogenic Viruses, Including Hepatitis A Virus and Human Rotavirus, from Oyster, Water, and Sediment Samples", Applied and Environmental Microbiology, vol. 54, No. 8, Aug. 1988; pp. 1983-1988.
Schwab et al., "Concentration and Purification of Beef Extract Mock Eluates from Water Samples for hte Detection of Enteroviruses, Hepatitis A Virus, and Norwalk Virus by Reverse Transcription-PCR", Applied and Environmental Microbiology, vol. 61, No. 2, Feb. 1995; pp. 531-537.
English translation of Israeli Office Action, dated Sep. 29, 2016, corresponding to Israeli Application No. 241540; 2 pages.
European Communication dated Jan. 2, 2017, corresponding to European Application No. 14 717 867.7; 5 pages.
European Communication and Supplemental Partial European Search Report, dated Nov. 14, 2016, corresponding to European Application No. 14859866.7, 9 pages.
European Communication dated Sep. 29, 2016, corresponding to European Application No. 10 817 867.4; 3 pages.
Korean Office Action (with English translation), dated Nov. 11, 2016, corresponding to Korean Application No. 10-2012-7009516; 12 total pages.
Israeli Office Action dated Jan. 16, 2017, corresponding to Israeli Application No. 218656; 2 pages.
Israeli Office Action dated Jan. 17, 2017, corresponding to Israeli Application No. 245875; 2 pages.
Mexican Office Action (No English translation available), dated Aug. 19, 2016, corresponding to Mexican Application No. MX/a/2013/003627; 3 pages.
Eurasian Office Action (with English translation), dated Dec. 19, 2016, corresponding to Eurasian Application No. 201390409/28; 4 total pages.
European Extended Search Report dated Feb. 15, 2017, corresponding to European Application No. 14833670.4; 9 pages.

(56) References Cited

OTHER PUBLICATIONS

"Ensure Plus HN", IP.COM Journal, IP.COM Inc., West Henrietta, NY, US, Feb. 9, 2002 (This document completes the disclosure of US2012/177629 with respect to the composition of the product Ensure Plus); 1 page.
Sackman et al., "Does Mixing Pancreatic Enzyme Microspheres (Pancrease) with Food Damage the Enteric Coating?", Journal of Pediatric Gastroenterology and Nutrition, Jan. 1, 1982; pp. 333-335.
Shlieout et al., "Administration of CREON Pancrelipase Pellets via Gastrostomy Tube is Feasible with no Loss of Gastrict Resistance or Lipase Activity—An In Vitro Study", Clinical Drug Investigation, vol. 31, No. 7, Jan. 1, 2011; pp. e1-e7.
English translation of a UAE Search Report and Examination Report issued by the UAE Patent Office dated Oct. 31, 2016, corresponding to UAE Application No. 743/2009; 15 total pages.
Canadian Office Action and Examination Search Report, dated Nov. 18, 2016, corresponding to Canadian Application No. 2,677,989; 3 total pages.
English translation of Chinese Office Action dated Jan. 20, 2017, corresponding to Chinese Application No. 201410059861.7; 4 total pages.
Australian Examination Report No. 1, dated Feb. 8, 2017, corresponding to Australian Application No. 2016204414; 5 pages.
Nakamura et al., "Effects of High-Lipase Pancreatin on Fecal Fat, Neutral Sterol, Bile Acid, and Short-Chain Fatty Acid Excretion in Patients with Pancreatic Insufficiency Resulting from Chronic Pancreatitis," International Journal of Pancreatology, Feb. 1998; vol. 23, No. 1; pp. 63-70.
G. J. Peschke, "Active Components and Galenic Aspects of Enzyme Preparations," Pancreatic Enzymes in Health and Disease, Springer-Verlag Berlin Heidelberg, 1991; pp. 55-64.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, (1997); pp. 498-506.
Felton and McGinity, "Influence of Insoluble Excipients on Film Coating Systems," Drug Development and Industrial Pharmacy, vol. 28, No. 3; (2002); pp. 225-243.
Nordmark pancreatin brochure, "Small but Smart—Enteric-coated microtablets," Nordmark—Products all over the World, (1999); (pp. 16-29) 7 total pages.
Handbook of Pharmaceutical Excipients, Fifth Edition, Edited by Raymond C. Rowe, et al. (Aug. 2005) 4 pages.
English translation of Pakistan Examination Report, corresponding to Pakistan Application No. 804/2010; (2011); 1 page.
Kahn, et al., Bovine Pancreatic LipaseI. II. Stability and Effect of Activators and Inhibitors, Journal of Dairy Science, vol. 59, No. 5, Apr. 1975; pp. 840-846.
Lombroso, (English translation) "About the Destruction of the Pancreatic Enzymes by Means of Heat and the Substances that Hamper Such Action", Archivio di Farmacologia Sperimentale e Scienze Affini, vol. XVIII, Laboratory of Physiology of the R. University of Rome; (1915); 14 total pages.
Novozymes-Savinase, novozymes, Rethink Tomorrow, Annex 1, A Hard-working, robust protease used to remove protein-based stains; Copyright 2008 Novozymes; 1 page.
Non-patent literature cited during the Appeal Procedure, relating to EP 1 335 706, (One Step Ahead, Granulation and drying for all types of products), Rotolab, (D24); Jun. 28, 2012; 8 pages.
Priority Document, Italian Patent No. ITMI20002456; "Microspheres of Pancreatic Enzymes with High Stability and Production Method Thereof," by Mario Maio; May 15, 2002; 25 pages.

Non-Patent Literature Document—"Aqueous Coating—Aquacoat ECD," FMC Biopolymer; (Jul. 2006); 12 pages.
Wikipedia Search Result for Mehl (Flour in English) (English translation also attached); printed from www.wikipedia.com on Feb. 2, 2017; 18 total pages.
European Communication dated Mar. 2, 2017, corresponding to European Application No. 15 178 147.3; 6 pages.
European Communication dated Aug. 2, 2017, corresponding to European Application No. 15 178 147.3; 8 pages.
Opekun, Jr. et al., "Lack of dose-response with Pancrease MT for the treatment of exocrine pancreatic insufficiency in adults," Blackwell Science Ltd., Aliment Pharmacol Ther (1997), vol. 11; pp. 981-986.
"Clinical Pharmacology and Biopharmaceutics Review(s)," Center for Drug Evaluation and Research, Apr. 23, 2010, Application No. 022523Orig1s000; 37 pages—Retrieved from the Internet: https:www.accessdata.fda.gov/drugsatfda_docs/nda/2010/022523orig1s000clinpharmr.pdf.
"Pancrease MT Capsules," Aug. 2005, Drug Reference Encyclopedia; 7 pages—Retrieved form the Internet: https://theodora.com/drugs/pancrease_mt_capsules_mcneil_consumer.html.
Non-Patent Literature document (2012), corresponding to EP 1 336 706, Main Request, Claims with revisions, relating to Appeal Procedure (E7); 1 pages.
Non-Patent Literature document (2012), Description, relating to EP 1 335 706, paragraphs [0022] through [0036] (p. 4), relating to the Appeal Procedure (E8); 1 page.
Non-Patent Literature document (2012), corresponding to EP 1 336 706, Main Request, Claims 1-7, relating to Appeal Procedure (E9); 2 pages.
Arbocel® Product Sheet, J. Rettenmaier & Bohne GmbH & Co. (JRS) (2012); 1 page.
European Communication dated Apr. 11, 2017, corresponding to Eurpoean Application No. 14859866.7; 1 page.
European Search Report dated Mar. 24, 2017, corresponding to European Application No. 14859866.7; 21 total pages.
Australian Examination Report, dated Apr. 10, 2017, corresponding to Australian Application No. 2016216662; 3 pages.
European Communication dated May 19, 2017, corresponding to European Application No. 10817867.4; 3 pages.
Japanese Office Action (no English translation availabel), dated Jul. 4, 2017, corresponding to Japanese Application No. 2016-196831.
Canadian Office Action and Examination Search Report, dated Aug. 16, 2017, corresponding to Canadian Application No. 2,812,862; 4 total pages.
Eurasian Office Action (with English Translation) dated Sep. 6, 2017, corresponding to Eurasian Application No. 201590835/28; 2 total pages.
Eurasian Office Action (with English Translation) dated Sep. 6, 2017, corresponding to Eurasian Application No. 201590836/28; 2 total pages.
European Communication dated Sep. 16, 2017, corresponding to European Application No. 14 815 008.9; 7 total pages.
Argentine Office Action dated Mar. 3, 2017, corresponding to Argentine Application No. P080100693; 6 pages (No English language translation available).
Taiwanese Office Action (with English translation), dated Feb. 16, 2017, corresponding to Taiwanese Aplication No. 102138934; 5 total pages.
Examination Report and Search Report issued by the Korean Intellectual Property Office dated Jul. 3, 2017, corresponding to AE Application No. UAE/P/0743/2009; 13 total pages.
Korean Office Action (with English Translation) dated Sep. 5, 2017, corresponding to Korean Application No. 10-2013-7010970; 12 total pages.

\* cited by examiner

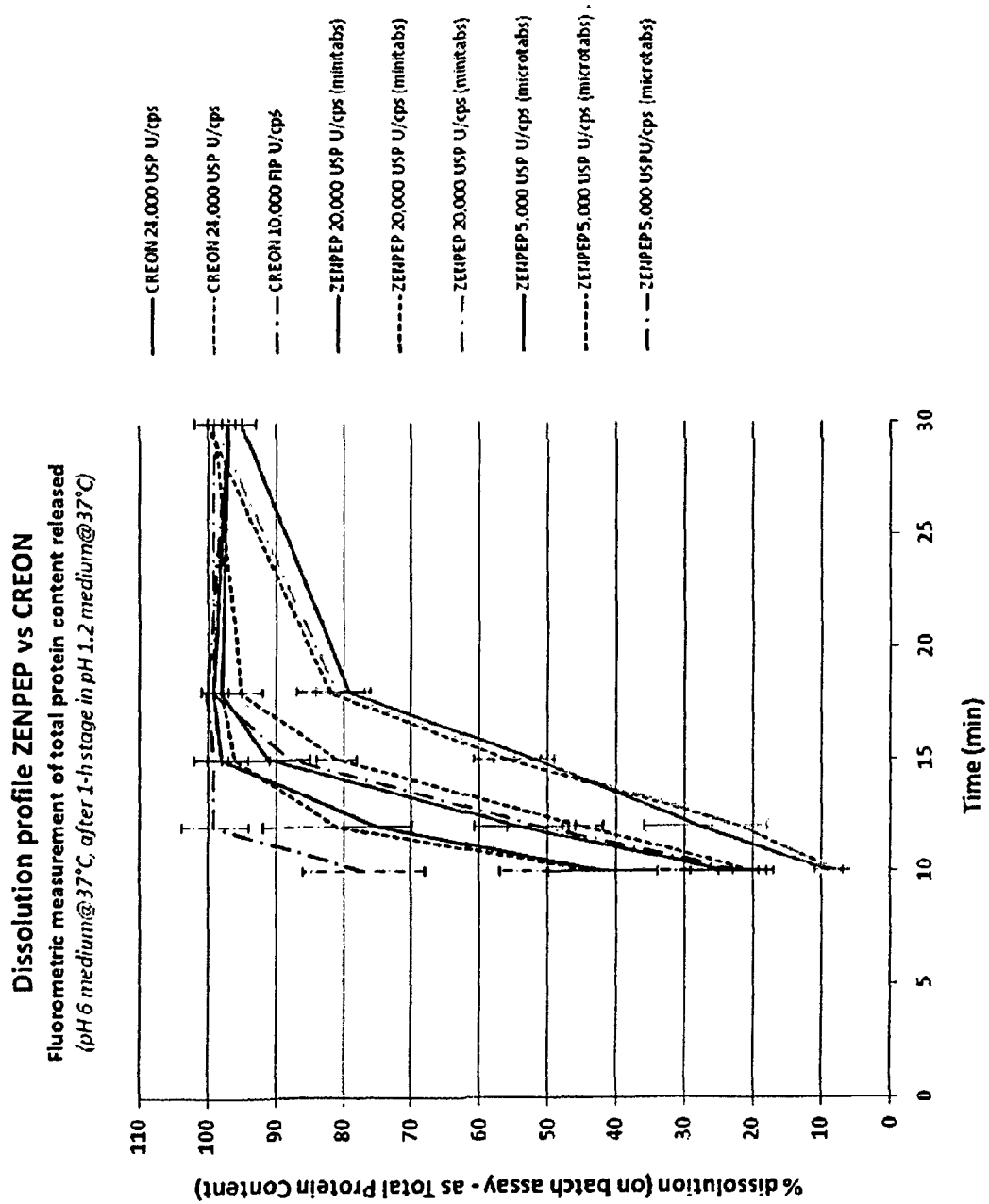

METHOD FOR DISSOLUTION TESTING OF SOLID COMPOSITIONS CONTAINING DIGESTIVE ENZYMES

FIELD OF THE INVENTION

The invention is directed to a process for measuring the amount of digestive enzymes released from a solid composition in a dissolution medium by fluorescence spectroscopy. The invention is also directed to a combined method for measuring both the dissolution and the gastroresistance of a solid composition comprising pancrelipase.

BACKGROUND OF THE INVENTION

A solid pharmaceutical composition or dosage form, such as a tablet or capsule, is generally composed of a mixture of active ingredient(s) and excipient(s). The reproducibility of the adsorption of an active ingredient (drug) from a solid composition form after oral administration depends on several factors such as the release of the drug from the composition and the dissolution or solubilization of the drug under physiological conditions. Because of the critical nature of the release of the drug from the composition and the dissolution or solubilization of the drug, a dissolution test is highly relevant to the prediction of the in-vivo performance of a drug. Drug approving authorities such as the FDA and EMA often require pharmaceutical companies to determine the drug release characteristics of any new pharmaceutical composition in order to obtain approval. These tests can also be required as an USP quality parameter, to assess batch-to-batch quality of a pharmaceutical composition, for accepting products, waiving bioequivalence requirements or supporting requests for other bioequivalence requirements than the recommended.

Various protocols have been developed for conducting the in-vitro dissolution tests and are routinely applied for both product development and quality control. Drug dissolution testing is mostly conducted using recommended compendia methods and apparatus, such as the U.S. Pharmacopoeia and the European Pharmacopoeia e.g. USP 34 <711> and EP 7.2, 2.9.3. Dissolution media typically used in such tests are for example water and buffers such as phosphate buffers or citrate buffers. Different types of dissolution apparatus, based on different stirring methods are available commercially and are recognized by the compendia methods. These apparatus include: paddle, basket, flow-through, and reciprocating cylinder. While exact procedures (protocols) and apparatus vary, all drug dissolution test methods involve placing the pharmaceutical composition or dosage form into a dissolution medium and applying some stirring to the dissolution medium in order to promote disintegration and dissolution of the drug under test.

The dissolution medium and the detection method for determining the amount of the released drug in the dissolution medium depends upon (is chosen according) the chemical nature of the drug, and physical and stability considerations are also of great importance in making the appropriate choices.

The test contained in the pancrelipase Delayed Release Capsule, USP Monograph for the determination of digestive enzymes release from pharmaceutical oral dosage forms, such as pancrelipase delayed released capsules is based on the specific measurement of lipase activity. Such method requires a long analysis time and is affected by several drawbacks. The main drawback is the instability of the marker-lipase in the dissolution medium, more precisely in the enteric stage buffer (pH 6.0) dissolution medium; the extent of lipase degradation needs to be established and a correction factor is then introduced into the dissolution calculation to account for lipase activity loss during the test. Furthermore, the complexity of the method (both in the reagent/substrates preparation and the analytical determination) increases significantly the variability of the results and worsens the intra/inter laboratories results' reproducibility. Moreover, lipase assay has a narrow linearity range (8-16 USP units/mL): this represents a significant limitation since the assay covers only capsule strengths ranging between 6,400 and 12,800 USP UI/capsule and therefore the single unit testing approach cannot be performed. The long analysis time in the current method limits the possibility of using it for determining a multi-point dissolution profile.

There are no method/procedure describing how to overcome these drawbacks for determining the release of digestive enzymes from a solid composition.

The digestive enzymes, such as pancrelipase and other pancreatic enzymes products (PEPs) can be administered to patients suffering from exocrine pancreatic insufficiency (EPI); the administration of digestive enzyme supplements allows patients to more effectively digest their food.

Exocrine pancreatic insufficiency (EPI), of which the FDA estimates that more than 200,000 Americans suffer, involves a physiological disorder wherein individuals are incapabile of properly digesting food due to a lack of digestive enzymes made by their pancreas. That loss of digestive enzymes leads to disorders such as the maldigestion and malabsorption of nutrients, which lead to malnutrition and other consequent undesirable physiological conditions associated therewith. These disorders are common for those suffering from cystic fibrosis (CF) and other conditions compromising the exocrine function of the pancreas, such as pancreatic cancer, pancreatectomy, and pancreatitis. The malnutrition can be life threatening if left untreated, particularly in the case of infants and CF patients, and the disorder can lead to impaired growth, a compromised immune response, and shortened life expectancy.

Digestive enzymes, such as pancrelipase and other pancreatic enzymes products (PEPs), can be administered to at least partially remedy EPI. The administered digestive enzymes provide for patients to be able to more effectively digest their food.

Pancreatic enzymes, which have been used in the treatment of EPI to compensate for lost digestive function, have been in use for more than 60 years. Their use until recently was not subject modern regulatory guidelines governing drug approvals based on safety, and efficacy, and manufacturing controls. Recently, pancreatic enzyme replacement therapies have become the subject of US and European regulatory authority initiatives that require that marketed pancreatic enzyme products to go through the current drug approval process in order to remain in commerce. Zenpep®, Creon® and Pancreaze® are three products that successfully went through the process set by the FDA and are approved for marketing in the United States. In other territories/countries where similar initiatives are still proceeding or have not been implemented as yet, a variety of pancreatic enzyme products are still available.

Capsules containing digestive enzymes such as pancrelipase have been developed for oral administration. However, if a patient is unable to swallow the capsules, each capsule can be opened and the contents sprinkled on a small amount of food, usually a soft, acidic food (such as commercially available applesauce) and administered orally to the patient with a spoon. Alternatively, such medications may be administered orally for infants and children, using a syringe device containing the contents suspended in a medium amenable to administration thereby.

The pancrelipase products are generally labeled as containing three enzyme classes, lipase, amylase, and protease, and the levels or potency of which are listed. These enzymes catalyze the hydrolysis of fats into glycerol and fatty acids, starch into dextrin and sugars, and proteins into amino acids and derived substances. Digestion is, however, a complex process involving many other enzymes and substrates that contribute to correct digestive functioning and producing the full range of digestive products. Other enzymes contained in pancrelipase include trypsin, carboxypeptidases, elastases, phospholipases, and cholesterases amongst others and various co-factors and coenzymes. These substances are produced naturally in the pancreas and also contribute to correct digestive functioning.

Pancrelipase is typically prepared from porcine pancreatic glands, although other sources can also be used, for example those described in U.S. Pat. No. 6,051,220, U.S. 2004/0057944, U.S. 2001/0046493, and WO2006044529, each of which is herein incorporated by reference in its entirety for all purposes.

Pancreatic enzymes show optimal activity under near neutral and slightly alkaline conditions. Under gastric conditions, pancreatic enzymes may be inactivated with a resulting loss in biological activity. Therefore, exogenously administered enzymes are generally protected against gastric inactivation and remain intact during their transit through the stomach and into the duodenum. Therefore, it is desirable to coat pancreatic enzymes. Pancreatic lipases are the most sensitive to gastric inactivation and are key enzymes in the treatment of malabsorption. Lipase activity is typically monitored to determine the stability of an enzyme composition containing lipase. The entire contents of U.S. Pat. No. 7,658,918 issued to Ortenzi et al. is expressly incorporated by reference in its entirety herein for all purposes, and describes stable digestive enzyme compositions and explains that certain particulate medications, administered orally, are designed to pass through the stomach of the patient and thereafter to release within the intestines. The administration of a proper dosage of such particulate medications to patients, particularly infants and children, should be as accurate as possible.

Unfortunately, no process for measuring the amount of digestive enzymes released from a solid pharmaceutical composition or dosage form with good precision and good sensitivity, and that is ready to be implemented in different laboratories has been described.

BRIEF SUMMARY OF THE INVENTION

The invention is directed to a process for measuring the amount of digestive enzymes released from a solid composition in a dissolution medium by fluorescence spectroscopy. The invention is also directed to a combined method for measuring both the dissolution and gastroresistance of a solid compositions comprising pancrelipase.

BRIEF DESCRIPTION OF THE FIGURES

FIG. 5. Dissolution profile of pancrelipase compositions (Zenpep® and Creon®).

DETAILED DESCRIPTION OF THE INVENTION

Figure 1:
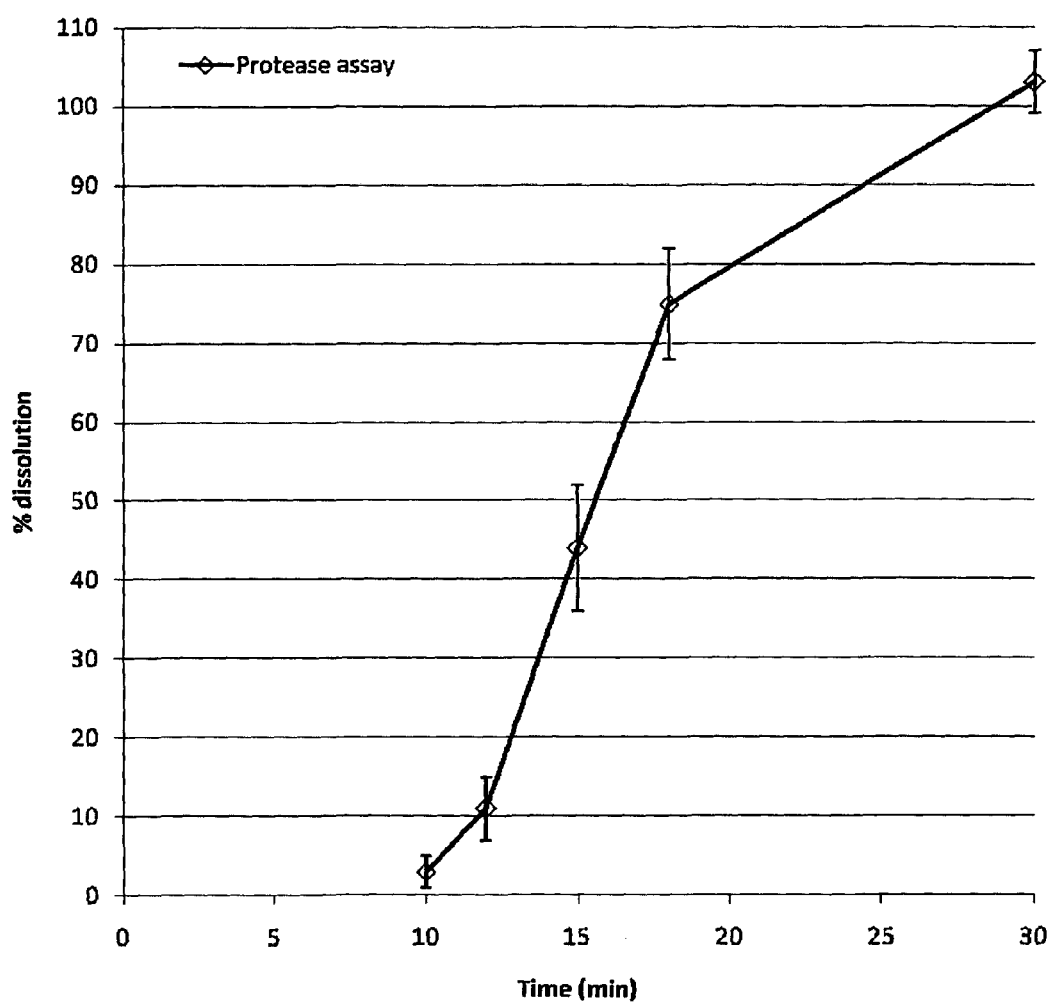
FIG. 1. Dissolution profile of pancrelipase beads (Zenpep® minitablets)—protease assay (mean curve).

The present invention is directed to a process for measuring the amount of digestive enzymes released from a solid composition in a dissolution medium by fluorescence spectroscopy. The amount is measured as % of digestive enzymes released from the solid composition or dosage form or single unit form.

In another embodiment of the process of the invention, the solid composition is a formulation comprising pancrelipase, more particularly it is an enteric coated pancrelipase composition comprising pharmaceutically inactive excipients.

In another embodiment the process comprises the steps of: (a) allowing the solid pancrelipase composition to release the digestive enzymes in a dissolution medium, (b) reading the fluorescence to measure the amount of digestive enzymes in the medium.

In another embodiment of the invention the dissolution medium is water, HCl solution, simulated gastric fluid, buffer solution, simulated intestinal fluid, or aqueous or buffer solution containing at least one surfactant.

In another embodiment the dissolution medium consists of at least two media that are applied sequentially. A two staged dissolution test may also be carried out with the present process. The first stage is an acid stage and the dissolution medium is an aqueous medium having acid pH, such as pH ranging from about 1 to about 4.5, or from about 1 to about 2, or of about 1.2. The second stage is performed in a second dissolution medium which is an aqueous buffer solution having pH above 5, or between about 5.5 and about 6.8, or about 6.

In the method according to the invention the technique used for detecting the digestive enzymes released from a composition in a dissolution medium is fluorescence spectroscopy.

Molecules have various states referred to as energy levels. Fluorescence spectroscopy is primarily linked to electronic and vibrational states. Generally, the species being examined has a ground electronic state, and an excited electronic state of higher energy. Within each of these electronic states there are various vibrational states. In fluorescence spectroscopy the species is first excited, by absorbing a photon, from its ground electronic state to one of the various vibrational states in the excited electronic state. The molecule then drops down to one of the various vibrational levels of the ground electronic state again, emitting a photon in the process. As molecules may drop down into any of several vibrational levels in the ground state, the emitted photons will have different energies, and thus frequencies. The fluorescence response of a protein is due to the presence of the amino acids containing aromatic moiety (tryptophan, tyrosine, or phenylalanine). Fluorescence response of a protein is generally obtained with an excitation wavelength of 280 nm. Most of the fluorescence emissions in the proteins are due to excitation of tryptophan residues, with a minor contribution of tyrosine and phenylalanine.

The fluorometric process herein disclosed is based on the measurement of total proteins content of digestive enzymes (pancrelipase, API) released in a dissolution medium from a composition or dosage form comprising said enzymes. The phrase "total proteins" used herein identifies all the proteins that are released by the drug product, that is all the proteins present in the starting solid composition such as lipases, proteases and amylases. In order to get a direct value of the released API, the standard preferably used in this method is prepared with the same lot of the tested drug product, but grinding and pouring it into the same dissolution medium to obtain the 100% API dissolved. Dissolution of the tested batch is measured as fraction percent towards the standard preparation.

The process of the present invention can be applied to pancrelipase solid compositions that may comprise pharmaceutically inactive excipients, such as any suitable oral dosage form that contains digestive enzymes. Non-limiting examples of suitable dosage forms include tablets, capsules, sachets or single units. In a particular embodiment, the dosage form is a capsule. Each dosage form contains digestive enzyme beads (also called units) of API (drug). For the present invention the digestive enzyme beads are any kind of particulates. The term "bead" includes granule, particle, tablet, sphere, minitablet, microtablet, microparticle, microsphere, minimicrosphere, microcapsule, and micropellet. The bead may be any suitable particle size or shape; particularly having a size range of about 50 to about 5,000 µm, more particularly they can have a nominal (e.g., mean) particle diameter in the range of about 2 to about 5 mm, or of less than about 2 mm, for example about 1-2 mm. "Minimicrosphere" have the smallest median size of 1.15 mm or "microtablet" have highest median size at 2.63 mm are also suitable for the present process. The beads can have an average size of less than about 800 µm, preferably less than 500 µm, preferably of about 400 µm to about 600 µm or of about 250 µm to about 500 µm. These beads may have a volume diameter (d(v,0.1) (defined as the diameter where 10% of the volume distribution is below this value and 90% is above this value) of not less than 400 µm and a volume diameter d(v,0.9), (defined as the diameter where 90% of the volume distribution is below this value and 10% is above this value) of not more than 900 µm.

All the digestive enzymes beads, more particularly pancrelipase enzyme beads, suitable for the preparation of pharmaceutical products may be coated by an enteric layer. In embodiments where pancrelipase cores are surrounded by an enteric coating the coating acts as a barrier, protecting the drug from the acidic environment of the stomach and substantially prevents the release of the medication before it reaches the small intestine. Suitable combinations of enteric coating compositions with other coating compositions can be used to provide the desired type of control over drug release or therapeutic effects. The enteric coating includes at least one enteric polymer and further excipients. The phrase "enteric polymer" means a polymer that protects the digestive enzymes from gastric contents, for example a polymer that is stable at acidic pH, but can break down rapidly at higher pH or a polymer whose rate of hydration or erosion is slow enough to ensure that contact of gastric contents with the digestive enzymes is relatively minor while it is in the stomach, as opposed to the remainder of the gastro-intestinal tract. Non-limiting examples of gastro-resistant polymers are cellulose acetate phthalate, hydroxypropylmethyl cellulosephthalate, hydroxypropyl methylcellulose acetate succinate, polyvinylacetate phthalate, copolymers of methacrylic acid, esters of methylmethacrylate, and shellac. These polymers are commercially available with different brand names, such as: Cellacefate® (cellulose acetate phthalate), Eudragit® L100, 5100, L30D, FS30D, L100-55 (copolymers of methacrylic acid), Aquateric® (cellulose acetate phthalate), Aqoat® (hydroxypropyl methylcelluloacetate succinate), HP55® (hydroxypropyl methylcellulose phthalate). Preferably the enteric coating comprises: 10-20 wt. % of at least one enteric polymer; wherein each said wt. % is based on the total weight of the coated particles. The coating may further comprises a lipophilic agent, such as a C6-C30 lipophilic low molecular weight molecule selected from the aliphatic carboxylic acids and alcohols, preferably a C14-C18 carboxylic acid or alcohol, such as stearic acid, myristic acid, myristic alcohol, or stearyl alcohol. Other optional ingredients of the coating are plasticizers, anti-tacking agents (such as talc, magnesium stearate, colloidal silicon dioxide and combinations thereof; further optionally a low viscosity ethylcellulose). Non-limiting examples of suitable plasticizers include triacetin, tributyl citrate, triethyl citrate, acetyl tri-n-butyl citrate, diethyl phthalate, dibutyl sebacate, polyethylene glycol, polypropylene glycol, castor oil, acetylated mono- and di-glycerides, cetyl alcohol, myristil alcohol, and mixtures thereof. The preferred plasticizer is a non-phthalate plasticizer or mixtures thereof.

The coated stabilized digestive enzyme particles can then be formulated into capsules. A particular dosage form of stabilized digestive enzyme particles is a capsule filled with enteric coated pancrelipase enzymes beads. Capsules containing the enterically coated pancrelipase enzymes comprised of hydroxypropylmethylcellulose having a water content of about 6 wt % or less are a particular embodiment for a dosage for; more particularly having a water content of about 4 wt % or less; further particularly having a water content of about 2 wt % or less.

The term "digestive enzyme" used herein denotes an enzyme in the alimentary tract which breaks down the components of food so that they can be taken or absorbed by the organism. Non-limiting examples of digestive enzymes include pancrelipase (also referred to as pancreatin), lipase, co-lipase, trypsin, chymotrypsin, chymotrypsin B, pancreatopeptidase, carboxypeptidase A, carboxypeptidase B, glycerol ester hydrolase, phospholipase, sterol ester hydrolase, elastase, kininogenase, ribonuclease, deoxyribonuclease, α-amylase, papain, chymopapain, glutenase, bromelain, ficin, β-amylase, cellulase, β-galactosidase, isomaltase, and mixtures thereof. They are obtained through extraction from pancreas or pancreatic juices or produced artificially or obtained from sources other than pancreas such as from microorganisms, bacteria, mold, fungi, plants or other animal tissues, genetically modified microorganisms, fungi or plants.

The terms "pancrelipase" or "pancrelipase enzymes" or "pancreatin" denotes a mixture of several types of enzymes, including amylase, lipase, and protease enzymes, or mixture thereof having pancreatic origin. Pancrelipase is commercially available, for example from Nordmark Arzneimittel GmbH, Scientific Protein Laboratories LLC or Sigma Aldrich; and similar extracts from porcine, bovine or other mammalian sources may be used. Examples of commercial pancrelipase formulations include Zenpep, Viokace, Ultrase, Creon, Pancreaze, and Panzytrat; more particularly, Zenpep capsule for oral administration contains enteric coated beads (1.8-1.9 mm for 750, 3,000, 5,000 USP lipase units, 2.2-2.5 mm for 10,000, 15,000, 20,000, 25,000 and 40,000 USP lipase units).

The term "lipase" denotes an enzyme that catalyzes the hydrolysis of lipids to glycerol and simple fatty acids. Examples of lipases suitable for the present invention include, but are not limited to animal lipase (e.g., porcine lipase), bacterial lipase (e.g., *Pseudomonas* lipase and/or *Burkholderia* lipase), fungal lipase, plant lipase, recombinant lipase (e.g., produced via recombinant DNA technology by a suitable host cell, selected from any one of microorganisms, bacteria, yeast, fungi, plants, insects or mammalian host cells in culture, or recombinant lipases which include an amino acid sequence that is homologous or substantially identical to a naturally occurring sequence, lipases encoded by a nucleic acid that is homologous or substantially identical to a naturally occurring lipase-encoding nucleic acid, etc.), synthetic lipase, chemically-modified lipase, and mixtures thereof. The term "lipids" broadly includes naturally occurring molecules including fats, waxes, sterols, fat-soluble vitamins (such as vitamins A, D, E and K), monoglycerides, diglycerides, triglyceridses, phospholipids, etc.

The term "amylase" refers to glycoside hydrolase enzymes that break down starch, for example α-amylases, β-amylases, γ-amylases, acid α-glucosidases, salivary amylases such as ptyalin, etc. Amylases suitable for use in the present invention include, but are not limited to animal amylases, bacterial amylases, fungal amylases (e.g., *Aspergillus* amylase, for example, *Aspergillus oryzae* amylase), plant amylases, recombinant amylases (e.g., produced via recombinant DNA technology by a suitable host cell, selected from any one of microorganisms bacteria, yeast, fungi, plants, insects or mammalian host cells in culture, or recombinant amylases which include an amino acid sequence that is homologous or substantially identical to a naturally occurring sequence, amylases encoded by a nucleic acid that is homologous or substantially identical to a naturally occurring amylase-encoding nucleic acid, etc.), chemically modified amylases, and mixtures thereof.

The term "protease" refers generally to enzymes (e.g., proteinases, peptidases, or proteolytic enzymes) that break peptide bonds between amino acids of proteins. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism. Non-limiting examples of proteases suitable for use in the present invention include serine proteases, threonine proteases, cysteine proteases, aspartic acid proteases (e.g., plasmepsin) metalloproteases and glutamic acid proteases. In addition, proteases suitable for use in the present invention include, but are not limited to animal proteases, bacterial proteases, fungal proteases (e.g., an *Aspergillus melleus* protease), plant proteases, recombinant proteases (e.g., produced via recombinant DNA technology by a suitable host cell, selected from any one of bacteria, yeast, fungi, plant, insect or mammalian host cells in culture, or recombinant proteases, which include an amino acid sequence that is homologous or substantially identical to a naturally occurring sequence, proteases encoded by a nucleic acid that is homologous or substantially identical to a naturally occurring protease-encoding nucleic acid, etc.), chemically modified proteases, and mixtures thereof.

The pancrelipase enzymes of the compositions or oral dosage forms analyzed in the present invention can include one or more lipases (i.e., one lipase, or two or more lipases), or one or more amylases (i.e., one amylase, or two or more amylases), or one or more proteases (i.e., one protease, or two or more proteases), as well as mixtures of these enzymes in different combinations and ratios.

Lipase activities in the compositions or dosage forms to be analyzed by the process of the present invention can be from about 650 to about 45,000 IU (USP method), from about 675 to about 825 IU, from about 2,700 to about 3,300 IU, from about 4,500 to about 5,500 IU, from about 9,000 to about 11,000 IU, from about 13,500 to about 16,500 IU, from about 18,000 to about 22,000 IU, from about 22,500 to about 27,500 IU, from about 36,000 to about 44,000 IU and all ranges and subranges there between. Lipase activities can be of about 750, about 3,000, about 4,200, about 5,000, about 6,000, about 10,000, about 10,500, about 15,000, about 16,800, about 20,000, about 21,000, about 24,000, or about 25,000, or about 40,000 IU (USP method) or multiple thereof. Amylase activities in the compositions or dosage forms can be from about 1,600 to about 6,575 IU (USP method), from about 6,000 to about 225,000 IU, for example from about 6,400 to about 26,300 IU, from about 10,700 to about 43,800 IU, from about 21,500 to about 87,500 IU, from about 32,100 to about 131,300 IU, from about 42,900 to about 175,000 IU, from about 53,600 to about 218,700 IU and all ranges and subranges there between. Protease activities in the compositions or dosage forms can be from about 1,250 to about 3,850 IU (USP method), from about 5,000 to about 130,000 IU, for example from about 5,000 to about 15,400 IU, from about 8,400 to about 25,700 IU, from about 16,800 to about 51,300 IU, from about 25,000 to about 77,000 IU, from about 33,500 to about 102,600 IU, from about 41,800 IU to about 128,300 IU and all ranges and subranges there between. Combined enzyme compositions include the following: (A) the lipase activity can range from about 675 to about 825 IU, the amylase activity from about 1,600 to about 6,575 IU, and the protease activity from about 1,250 to about 3,850 IU (USP method); (B) the lipase activity can range from about 2,700 to about 3,300 IU, the amylase activity from about 6,400 to about 26,300 IU, and the protease activity from about 5,000 to about 15,400 IU (USP method); (C) the lipase activity can range from about 4,500 to about 5,500 IU, the amylase activity from about 10,700 to about 43,800 IU, and the protease activity from about 8,400 to about 25,700 IU (USP method); (D) the lipase activity can range from about 9,000 to about 11,000 IU, the amylase activity from about 21,500 to about 87,500 IU, and the protease activity from about 16,800 to about 51,300 IU (USP method); (E) the lipase activity from about 13,500 to about 16,500 IU, the amylase activity from about 32,100 to about 131,300 IU, and the protease activity from about 25,000 to about 77,000 IU (USP); (F) the lipase activity can range from about 18,000 to about 22,000 IU, the amylase activity from about 42,900 to about 175,000 IU, and the protease activity from about 33,500 to about 102,600 IU (USP); and (G) the lipase activity can range from about 22,500 to about 27,500 IU, the amylase activity from about 53,600 to about 218,700 IU, and the protease activity from about 41,800 IU to about 128,300 IU (USP). Also the lipase activity in the compositions or dosages forms to be analyzed by the process of the invention can range from about 5,000 PhEur lipase units to about 40,000 PhEur lipase units, it may be about 5,000, or about 10,000, or about 15,000 or about 20,000 or about 30,000 or about 40,000 PhEur lipase units.

In another embodiment of the present invention also single units containing a fraction of the above listed amylase activities can also be analyzed with the present procedure.

In another embodiment of the present invention also single units containing a fraction of the above listed amylase activities can also be analysed with the present process.

The ratio of amylase/lipase activities in the compositions or dosages forms can range from about 1 to about 10, such as from about 2.38 to about 8.75 (enzymatic assay is performed according to USP). This ratio can range from about 1 to about 8, such as from about 1.86 to about 5.13 (enzymatic assay is performed according to USP), or the ratio can be about 1, about 2, about 3, about 4, about 5, about 6, about 7, about 8, about 9, or about 10.

The inactive ingredients of the product include croscarmellose sodium, hydrogenated castor oil, colloidal silicon dioxide, microcrystalline cellulose, magnesium stearate, hypromellose phthalate, talc, and triethyl citrate. Every dose of Aptalis Pharma's preparations provides patients and physicians with a consistent amount of the main pancreatic enzymes lipase, protease, and amylase due to their highly stable formulation. Capsules can be opened and the content split to individually titrate the dose.

Another embodiment of the invention, the process comprises the steps of: (a) allowing the solid pancrelipase composition to release the digestive enzymes in the dissolution medium, (b) reading the fluorescence to detect the enzymes and measure the amount of digestive enzymes in the medium. The dissolution test is carried out using the dissolution equipments described in the compendia USP or EMA methods or using all these equipments and protocols that are known and applied by the experts of the field. The dissolution medium is chosen among different solutions suitable for the testing of total proteins dissolution such as water, HCl solutions, simulated gastric fluids, buffer solutions, simulated intestinal fluids, aqueous or buffer solutions containing surfactants. Buffer solutions may be for example phosphate buffers or citrate buffers.

In a particular embodiment, the dissolution medium consists of at least two dissolution media that are used sequentially (two stages). The first dissolution medium is an aqueous medium has an acid pH between about 1 and 4.5, particularly between about 1 and about 2, more particularly at a pH of about 1.2 (acid stage) and the second dissolution medium is aqueous solution having pH of above about 5.0, particularly between about 5.5 and about 6.8, more particularly at a pH of about 6 (buffer enteric stage).

In another embodiment of the invention the first dissolution medium is an aqueous medium having pH between about 1 and about 4.5 and the second dissolution medium is aqueous buffer solution having pH above about 5.

In another embodiment the first dissolution medium is an aqueous medium having pH between about 1 and about 4.5 and the second dissolution medium is aqueous buffer solution having pH between about 5.5 and about 6.8.

In another embodiment of the invention the first dissolution medium is an aqueous medium having pH between about 1 and about 2 and the second dissolution medium is aqueous buffer solution having pH above about 5.

In another embodiment of the invention the first dissolution medium is an aqueous medium having pH between about 1 and about 2 and the second dissolution medium is aqueous buffer solution having pH between about 5.5 and about 6.8.

In another embodiment of the invention the first dissolution medium is an aqueous medium having pH of about 1.2 and the second dissolution medium is aqueous buffer solution having pH of about 6.

In a further embodiment the process comprises the steps of a) adding the solid pancrelipase composition in the first dissolution medium (acid stage), b) transferring the suspension to the second dissolution medium (enteric stage), c) allowing the release of the digestive enzymes, d) sampling aliquots of dissolution medium, e) reading fluorescence at 346 nm, d) calculating the amount of digestive enzymes released. Calculation is performed as reported in the Examples.

When applying dissolution tests to a drug product, USP requires the calculation of "Q" values. These Q values are correlated to the labeled potencies and the current acceptance criteria are fixed as 75% of the lipase labeled activity.

The fluorometric process of the present invention, even though not specific for enzymatic activity measurement, shows full correlation to enzymatic dissolution profiles, thus demonstrating that the total proteins release is strictly correlated to the enzymes release. Therefore "Q" value can be calculated for the present method in the following way: Q" value in the dissolution method with fluorometric measurement:

$$Q = \frac{\%\ \text{dissolution} \times \text{batch lipase assay}\ (USP\text{-}U/cps)}{\text{labeled lipase Activity}\ (USP\text{-}U/cps)}$$

where: % dissolution is % of API released, calculated as indicated in the analytical procedure; batch lipase assay is the batch lipase activity; labeled lipase activity: lipase activity indicated in the drug product label.

While the fluorometric method disclosed herein showed full correlation with enzymatic activity measurement while conducting the buffer enteric stage dissolution test of pancrelipase compositions and is therefore proposed as method substituting the lipase activity enzymatic test, this method cannot detect any gastroresistance problem occurring during the dissolution at the acidic stage, since total proteins fluorometric measurement is not affected by acid permeation through the membrane as it is lipase assay. The lipase activity is strongly decreased in case acidic juice permeates through the protective membrane. The current USP test (lipase activity measurement) cumulates at the end of the dissolution at the buffer enteric stage the effects of potential weak gastro-resistance at the acidic stage with lipase dissolution and degradation phenomena, occurring at the buffer enteric stage.

Therefore, another embodiment of the present invention is a process for measuring the amount (%) of digestive enzymes released from a solid pancrelipase composition in dissolution medium by fluorescence spectroscopy combined with a gastroresistance test, wherein the gastroresistance is measured by determining the residual lipase activity of the product by the specific lipase assay method, after acidic medium exposure (acid stage). In this embodiment the two tests (dissolution FL test and gastoresistant GR test) can be carried out in each order.

FL test: the dissolution test performed in two stages (acid and enteric). In the first acid stage dissolution medium is an aqueous medium having acid pH between about 1 and about 4.5, preferably pH between about 1 and about 2, preferably a pH of about 1.2 (acid stage); in the second enteric stage the dissolution medium is aqueous buffer solution having pH above about 5, preferably pH between about 5.5 and about 6.8, preferably pH of about 6 (buffer enteric stage). The gastro-resistance test is performed in aqueous medium having acid pH between about 1 and about 4.5, preferably pH between about 1 and about 2, preferably pH of about 1.2. The fluorometric test measures the digestive enzymes (API or drug) released at the end of the enteric stage; for the acceptance criteria, the Q value can be calculated by the ratio batch released lipase activity/labeled lipase activity.

GR test: the gastroresistance test is performed under the conditions of the acid stage of the dissolution test (the dissolution medium is an aqueous solution having acidic pH between about 1 and about 4.5, particularly at pH between about 1 and about 2, more particularly at a pH of about 1.2, where the % gastroresistance is measured by the determination of residual lipase activity of the product, after exposure to the acidic medium, with the lipase assay method the acceptance criteria will be those indicated for the acid stage of delayed-release dosage forms in USP.

From the foregoing description and the experimental part, it can be seen that the present fluorimetric process of analysis provides several important advantages.

The invention provides a simple and fast procedure because the time required for reagents preparation is significantly reduced and no specific analytical expertise in enzyme assay is required. Hence, the analytical transfer is very easy. The proposed method is easier and faster to be performed than the lipase assay and the time required for reagents preparation is significantly reduced.

The marker (total proteins) is stable in the dissolution medium and therefore no correction factor for compensation for degradation (as required in the lipase assay method) is needed in the calculation. In fact, the marker assayed in the fluorometric measurement (total proteins) shows less than 3% degradation after 30 min in enteric stage medium buffer pH 6, at 37° C.; whereas the lipase enzymatic activity measured with the current method shows about 11% degradation in the enteric stage medium buffer pH 6, at 37° C.

The new method is also precise and has good sensitivity such that the quantitation limit/linearity range is suitable also for single unit testing. The fluorometric method exhibits better performance characteristics than the lipase enzymatic assay in terms of working concentration, which is 0.3 lipase USP units≈3 µg pancrelipase/mL; which is about ⅕₀ of the working concentration of lipase assay; the linearity range is 10-200% of working concentration; the precision is not more than 2.0% either for repeatability and intermediate precision (as measured in the dissolution results of six different lots of pancrelipase formulations, Zenpep®).

Moreover, with such process a testing multi-point (>3) dissolution profile can be obtained.

It is also shown in the experimental part that the invented fluorometric non-specific procedure of detection of total proteins content is equivalent, in terms of performance, to the two enzyme-specific assays based on protease activity and on lipase activity (current compendia method), on the basis of a the comparison of dissolution profiles obtained using the three measurement methods.

It is to be understood that both the foregoing general description and the following detailed description are exemplary, but are not restrictive, of the invention.

EXAMPLES

Equipments, Materials and Methods

Equipment: LS 50B Fluorescence Spectrometer (Perkin Elmer), LS 55 Fluorescence Spectrometer (Perkin Elmer), Lambda 20 UV-VIS Spectrometer (Perkin Elmer), 786 Titrando Potentiometric Titration System (Metrohm), VK-7025 dissolution bath (Vankel), Premier 5100 dissolution bath (Distek), USP Apparatus 1—basket (for acid stage); USP Apparatus 2—paddle (for enteric stage).

Reagents for dissolution test. Acid stage medium (pH 1.2): Place 2.00 g of sodium chloride in 800 mL purified water and stir until complete solubilization. Add 7 mL 37% HCl and mix. Adjust the pH of the solution to 1.20±0.05 with 1 N HCl or 1 N NaOH. Dilute to 1000 mL with purified water; check the pH and adjust to 1.20±0.05 with 1 N HCl or 1 N NaOH, if needed.

Reagents for dissolution test. Enteric stage medium (pH 6.0): Place 9.20 g monobasic potassium phosphate and 2.00 g sodium chloride in 800 mL purified water and stir until complete solubilization. Adjust the pH of the solution to 6.00±0.05 with 1 N NaOH. Dilute to 1000 mL with purified water; check the pH and adjust to 6.00±0.05 with 1 N HCl or 1 N NaOH, if needed.

All examples are carried out using enterically coated pancrelipase beads, either pancrelipase minitablets (MTs) or microtablets (MCTs), which are a blend of pancrelipase raw material and excipients (e.g., croscarmellose sodium, hydrogenated castor oil, colloidal silicon dioxide, microcrystalline cellulose, and magnesium stearate) coated with the enteric polymer hypromellose phthalate (HP55); these MTs and MCTs are contained in HPMC capsules and are marketed under the name Zenpep®. The skilled artisan will recognize that alternative enteric polymers and excipients may be used in the enterically coated pancrelipase beads.

The measurement of lipolytic activity is carried out with a method based on the compendia procedure of lipase assay described in the pancrelipase USP monograph, which is based on the titration, by means of pH-stat method, of the free fatty acids formed from the hydrolysis of esterified fatty acids in the substrate used (olive oil). It is based on the following principle: lipase catalyses the hydrolysis of the triglycerides which leads to the formation of free fatty acids (FFA). The titration of the formed FFA according to time provides for the determination of the enzymatic activity of lipase, which can be expressed in units: 1 U=1 µmole of formed FFA per minute. The reaction occurs by maintaining a steady pH value through an experimental system that provides for the addition of NaOH (titrant) when the pH value changes compared to a fixed value (pHstat method). The quantity of added titrant according to time corresponds to the quantity of FFA formed by the lipase action on the triglycerides. Provided to work with a suitable quantity of substrate and under experimental conditions where the enzyme is stable, a linear kinetics for the FFA formation according to time can be obtained. The curve slope {added titrant=f(volume (mL)/time (minutes))} gives the lipase enzymatic activity.

The measurement of proteolytic activity is carried out according to the compendia procedure described in the pancrelipase USP monograph.

Example 1

Preparation of Standard Solution of Drug Product

The standard solution is prepared with the same lot of drug product present in the dosage form under analysis. An amount of pancrelipase beads (Zenpep® minitabs or microtabs) equivalent to 7,000 USP lipase units, is accurately weighed, in a mortar. Add 5-6 mL of enteric stage medium and grind until a complete dispersion of the product is obtained. The suspension is transferred into a 500 mL volumetric flask. The mortar is rinsed 2-3 times with few mL of enteric stage medium and the liquid is transferred into the 500 mL volumetric flask. Enteric stage medium is added into the volumetric flask up to final total 500 mL and the mixture is stirred for 10 minutes. The aliquots that are sampled from the dissolution medium are further diluted 1:50 with enteric stage medium. With this dilution the final concentration of API is about 0.3 USP lipase units (about 3 µg pancrelipase/ mL). This last dilution is carried out in the dissolution test—endpoint only and in the dissolution test—multipoint (dissolution profile).

Example 2

Dissolution Test 800 mL of the acid stage medium is added in each vessel of the dissolution bath equipped with basket apparatus; the dissolution medium is equilibrated at 37° C. An amount of pancrelipase beads (Zenpep minitabs or microtabs) equivalent to 11,200 USP lipase units (14 USP lipase units/mL) is weighted and six independent samples are prepared in this way and placed in the baskets. The apparatus is operated at 100 rpm. After 1 hour the baskets are removed from the medium, rinsed with a few milliliters of water and the content of each basket is transferred in a corresponding vessel containing 800 mL of the enteric stage medium at 37° C. of the dissolution bath equipped with paddle apparatus. The apparatus is operated at 100 rpm. After 30 min an aliquot of the dissolution medium from each vessel is sampled for measuring the API released. In the determination of the dissolution profile, 2.5 mL aliquots of the dissolution medium in the enteric stage are sampled at 10, 12, 15, 18, 30 min; no medium replacement is done during the test, the loss of volume being taken into account in the calculation by the correction factors below.

TABLE 1

Correction factors (FC) for the calculation of dissolution profile

| Timepoint (min) | Aliquot volume (mL) | Medium volume (mL) | Correction factor |
|---|---|---|---|
| 10 | 2.5 | 800.0 | 1.00000 |
| 12 | 2.5 | 797.5 | 0.99688 |
| 15 | 2.5 | 795.0 | 0.99375 |
| 18 | 2.5 | 792.5 | 0.99063 |
| 30 | 2.5 | 790.0 | 0.98750 |

Example 3

Determination of the Digestive Enzymes (API, Active Ingredient) Released in the Dissolution Test by Fluorescence Spectroscopy (Total Proteins Assay)

Each aliquot of dissolution medium sampled from each basket as described in Example 2 is diluted 1:50 with the enteric stage medium. The diluted solutions are read in the fluorescence spectrometer with the following operative parameters: 1 cm pathlength quartz cuvette; excitation wavelength: 280 nm; emission wavelength (measurement): 346 nm, excitation slit: 6.0. The target concentration of the marker (API=pancrelipase; 100% released) at the endpoint:

0.3 USP lipase units/mL or about 3 µg pancrelipase/mL; is obtained with the following calculation:

$$\frac{\text{Lipase } USP \text{ units in the vessel}}{\text{Potency of Drug Product (Lipase } USPU/\text{mg})} \times$$

$$\frac{0.72(\% \, APIin \, DP \, \text{formulation})}{\text{Dilution(ml)}} \times 1000 \, (\mu g/mg)$$

The amount of released API is determined against a standard solution prepared with the same lot of the drug product as described in Example 1.

For dissolution test—the endpoint the calculation is done with the following formula.

$$\% \, API \text{ released} = \frac{E_{SMP} \times W_{STD} \times V_{SMP}}{E_{STD} \times W_{SMP} \times V_{STD}} \times 100$$

For dissolution test—the multipoint (dissolution profile) the calculation is done with the following formula:

$$\% \, API \text{ released} = \frac{E_{SMP} \times W_{STD} \times V_{SMP}}{E_{STD} \times W_{SMP} \times V_{STD}} \times 100 \times FC$$

Wherein: $E_{SMP}$ is fluorescence reading (emission at 346 nm) of the sample, subtracted of the blank; $E_{STD}$ is fluorescence reading (emission at 346 nm) of the standard, subtracted of the blank; $W_{SMP}$ is the sample weight (mg); $W_{STD}$ is the standard weight (mg); $V_{SMP}$ is the dilution volume of the sample (mL); $V_{STD}$ is the dilution volume of the standard (mL); FC is the correction factor (see Table 1).

$$\frac{\text{Lipase } USP \text{ units in the vessel}}{\text{Potency of Drug Product(Lipase } USPU/\text{mg})} \times$$

$$\frac{0.72(\% \, APIin \, DP \, \text{formulation})}{\text{Dilution(ml)}} \times 1000 \, (\mu g/mg)$$

Example 4

Validation Study of the Total Proteins Assay by Fluorescence Spectroscopy

The performance characteristics of the fluorometric determination of total proteins content in the API released from pancrelipase composition (Zenpep® formulation) in the dissolution test is evaluated by the following parameters: specificity, linearity, accuracy, precision, quantitation limit, stability of sample and standard solution, demonstration of the completeness of the extraction in the preparation of standard solution and the results are summarized in Table 2.

TABLE 2

| Validation data of fluorimetric method | | | |
|---|---|---|---|
| Parameter | Test description | Result | Comments |
| Specificity | Interference of formulation excipients: excipient matrix vs API readings | 1.6% | Three independent samples per each group, 100% of target conc. Results are expressed as (reading excipients/ reading API) × 100 |

TABLE 2-continued

Validation data of fluorimetric method

| Parameter | Test description | Result | Comments |
|---|---|---|---|
| Linearity | 0.3-6.7 µg pancrelipase/mL (0.03-0.65 USP lipase U/mL) | Regression equation: y = 5.52 + 68.75x $r^2$ = 0.9992 | Six conc. levels, two independent samples each level: 10-25-50-100-150-200% of the target conc (~3 µg API/mL). |
| Accuracy | 0.3-6.6 µg pancrelipase/mL | Conc. level % recovery 0.3 µg/mL 107.8 1.6 µg/mL 106.8 3.3 µg/mL 104.8 4.9 µg/mL 103.1 6.6 µg/mL 104.5 | Five conc. levels, three independent samples each level: 10-50-100-150-200% of target conc (~3 µg API/mL) |
| Precision: repeatability | Dissolution test is performed on six lots of pancrelipase formulations, n = 6 each lot | CV in the range 1.1-2.0% for all tested lots | |
| Precision: Intermediate Precision | Dissolution test is performed on six lots of Zenpep ® formulations, n = 6 each lot; 2 runs each lot | CV in the range 1.0-1.9% for all tested lots | No statistically significant differences in the data from the two runs (t test) |
| Limit of Quantitation | 0.3 µg pancrelipase/mL; Precision of readings of six independent solns. | CV = 1.8% | LOQ value is determined by the regression equation |
| Completeness of the extraction in the preparation of standard solution | Determination of the recovery of STD prepared with one lot of each Zenpep ® formulation, three independent samples/lot | Recovery STD minitabs: 99.3% Recovery STD microtabs: 102.4% | Recovery is determined against the same API raw material that is contained in the formulations tested |
| Stability of Sample in dissolution test conditions (=stability of the marker) | Six independent preparations of artificial sample (API + formulation excipients), in the conditions of dissolution test (enteric stage buffer, 37° C., 100 rpm) | After 30 min: −2.7% after 60 min: −4.5% | Comparison with initial response (time 0 = after 5 min from the start of dissolution test) |
| Stability of sample at the end of dissolution test, solutions stored at r.t. | Six independent samples of both Zenpep ® formulations, solutions in enteric stage buffer withdrawn at the endpoint of dissolution test and stored at r.t. before the final 1:50 dilution | After 2 hours: $SMP_{MINITABS}$ = −0.9% $SMP_{MICROTABS}$ = −1.7% after 6 hours: $SMP_{MINITABS}$ = −1.7% $SMP_{MICROTABS}$ = −2.4% | Comparison with initial response (time 0 = endpoint of the dissolution test) |
| Stability of standard solution | Standard solutions prepared with both Zenpep ® formulations; three independent samples/formulation | After 2 hours: $STD_{MINITABS}$ = −0.9% $STD_{MICROTABS}$ = −1.0% after 6 hours: $STD_{MINITABS}$ = −1.6% $STD_{MICROTABS}$ = −1.4% | Comparison with initial response (time 0) |

With the validation data obtained, it is here shown that the proposed fluorometric method for the determination of total proteins content in the dissolution test of pancrelipase dosage forms (Zenpep® formulation) is suitable for the intended use.

Example 5

Dissolution Profile of Pancrelipase Beads (Zenpep® Minitabs with Three Measurement Methods: Total Proteins Content by Fluorescence Spectroscopy (Non-Specific Assay), the Proteolytic Activity by Protease Assay (Enzyme Specific Assay), and the Lipolytic Activity by Lipase Assay (Enzyme Specific Assay)

The dissolution test is performed according to method described above (see Example 2), by sampling 2.5 mL aliquots at: 10, 12, 15, 18 and 30 min. No medium replacement is done during the test. The comparison of the three processes is performed according to the SUPAC approach (Guidance for Industry "SUPAC MR: Modified release solid oral dosage forms. Scale-up and postapproval changes: chemistry, manufacturing, and controls, in vitro dissolution testing, and in vivo bioequivalence documentation" Center for Drug Evaluation and Research (CDER), September 1997) for the demonstration of similarity of dissolution profiles by means of f2 test; to generate the required number of data for each of the three measurement methods twelve independent samples (sample=amount of pancrelipase beads, Zenpep® minitabs equivalent to 11,200 UI) are analyzed, in groups of three samples per run, four runs in total.

Example 5.1

Dissolution Profile of Pancrelipase Beads (Zenpep® Minitablets) by Protease Assay The individual dissolution values and overall average at each tested timepoint are summarized in Table 3; the mean curve is shown in FIG. 1.

TABLE 3

Dissolution profile data (protease assay)

| min | % dissolution (n = 12) | | | | | | | | | | | | Mean | SD | CV (%) |
|---|---|---|---|---|---|---|---|---|---|---|---|---|---|---|---|
| | 1 | 2 | 3 | 4 | 5 | 6 | 7 | 8 | 9 | 10 | 11 | 12 | | | |
| 10 | 0 | 5 | 7 | 2 | 6 | 5 | 3 | 1 | 3 | 4 | 2 | 3 | 3 | 2 | 66.7 |
| 12 | 3 | 10 | 13 | 14 | 18 | 13 | 6 | 10 | 9 | 14 | 10 | 14 | 11 | 4 | 36.4 |
| 15 | 32 | 36 | 54 | 56 | 46 | 49 | 37 | 41 | 37 | 49 | 40 | 49 | 44 | 8 | 18.2 |
| 18 | 61 | 69 | 70 | 83 | 79 | 79 | 71 | 74 | 78 | 85 | 71 | 77 | 75 | 7 | 9.3 |
| 30 | 100 | 95 | 100 | 106 | 106 | 105 | 107 | 101 | 108 | 105 | 103 | 101 | 103 | 4 | 3.9 |

Example 5.2

Figure 2:
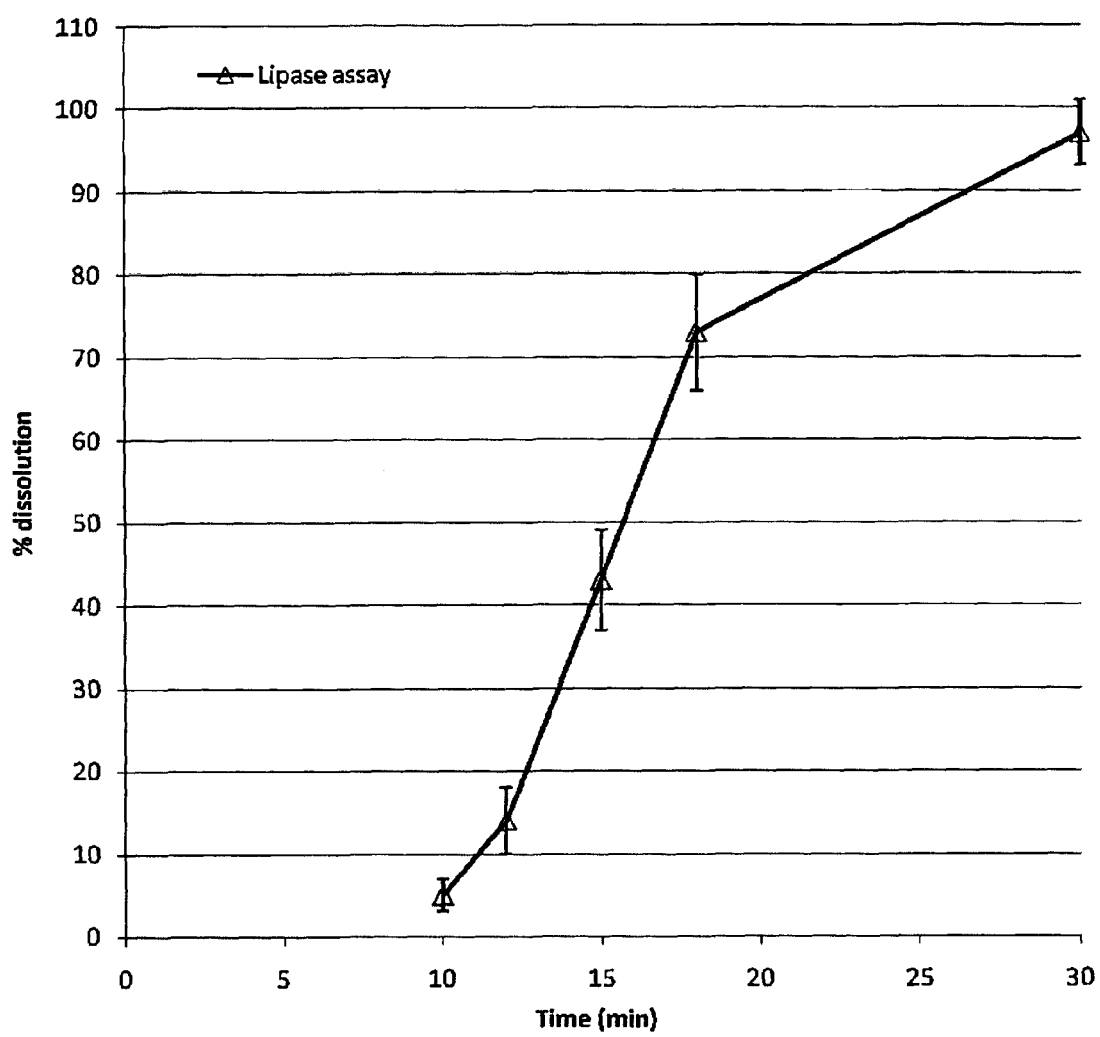
FIG. 2. Dissolution profile of pancrelipase beads (Zenpep® minitablets)—lipase assay (mean curve).

Dissolution Profile of Pancrelipase Beads (Zenpep® Minitablets) by Lipase Assay The individual dissolution values and overall average at each tested timepoint are summarized in Table 4; the mean curve is shown in FIG. 2. The correction factor of 1.125 is used in the calculation to compensate the lipase degradation during the dissolution test.

TABLE 4

Dissolution profile data (lipase assay)

| time (min) | % dissolution (n = 12) | | | | | | | | | | | | Mean | SD | CV(%) |
|---|---|---|---|---|---|---|---|---|---|---|---|---|---|---|---|
| | 1 | 2 | 3 | 4 | 5 | 6 | 7 | 8 | 9 | 10 | 11 | 12 | | | |
| 10 | 9 | 5 | 5 | 6 | 6 | 6 | 3 | 6 | 6 | 2 | 3 | 0 | 5 | 2 | 40.0 |
| 12 | 23 | 14 | 15 | 12 | 14 | 11 | 12 | 14 | 15 | 9 | 14 | 9 | 13 | 4 | 30.8 |
| 15 | 55 | 36 | 46 | 38 | 44 | 33 | 41 | 43 | 52 | 41 | 44 | 40 | 42 | 6 | 14.3 |
| 18 | 81 | 70 | 75 | 61 | 73 | 61 | 77 | 78 | 81 | 72 | 75 | 72 | 73 | 7 | 9.6 |
| 30 | 102 | 99 | 101 | 90 | 96 | 96 | 92 | 96 | 101 | 98 | 98 | 98 | 97 | 4 | 4.1 |

Example 5.3

Figure 3:
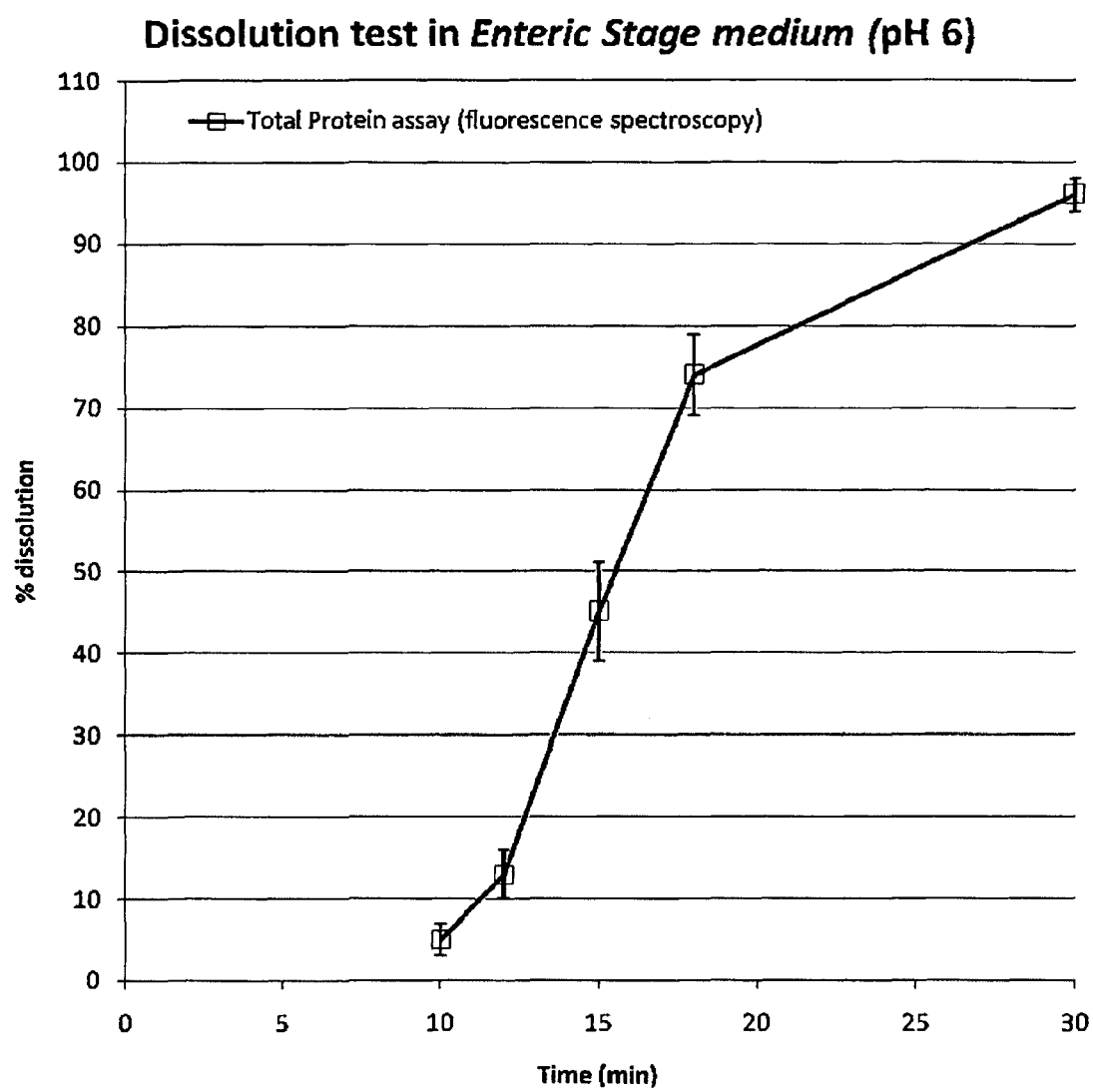
FIG. 3. Dissolution profile of pancrelipase beads (Zenpep® minitablets)—total proteins assay by fluorescence spectroscopy (mean curve).

Dissolution Profile of Pancrelipase Beads (Zenpep® Minitablets) by Fluorimetric Determination of Total Proteins Content The individual dissolution values and overall average at each tested timepoint are summarized in Table 5; the mean curve is shown in FIG. 3.

TABLE 5

Dissolution profile data (total proteins assay by fluorescence spectroscopy)

| time (min) | % dissolution (n = 12) | | | | | | | | | | | | Mean | SD | CV |
|---|---|---|---|---|---|---|---|---|---|---|---|---|---|---|---|
| | 1 | 2 | 3 | 4 | 5 | 6 | 7 | 8 | 9 | 10 | 11 | 12 | | | |
| 10 | 5 | 3 | 4 | 8 | 4 | 6 | 7 | 4 | 5 | 5 | 3 | 5 | 5 | 2 | 40.0% |
| 12 | 12 | 10 | 11 | 14 | 11 | 16 | 19 | 15 | 15 | 16 | 9 | 12 | 13 | 3 | 23.1% |
| 15 | 46 | 42 | 45 | 50 | 41 | 51 | 57 | 47 | 45 | 50 | 37 | 37 | 45 | 6 | 13.3% |
| 18 | 74 | 69 | 71 | 77 | 74 | 80 | 80 | 74 | 72 | 77 | 67 | 65 | 74 | 5 | 6.8% |
| 30 | 99 | 96 | 96 | 99 | 99 | 97 | 98 | 96 | 95 | 95 | 93 | 93 | 96 | 2 | 2.1% |

Example 5.4

Comparison of the Dissolution Profiles Obtained with the Three Measurement Methods The average dissolution data of pancrelipase beads (Zenpep® minitablets), measured at each timepoint with the three assay methods, are summarized in Table 6.

TABLE 6

Average dissolution data of pancrelipase beads (Zenpep ® minitablets) obtained with lipase assay, protease assay, and fluorimetric determination of total proteins

| | % dissolution (average ± SD of n = 12 independent samples) | | | | | | | | | |
|---|---|---|---|---|---|---|---|---|---|---|
| Test | 10 min | | 12 min | | 15 min | | 18 min | | 30 min | |
| protease assay | 3 ± 2 | CV = 67% | 11 ± 4 | CV = 36% | 44 ± 8 | CV = 18% | 75 ± 7 | CV = 9% | 103 ± 4 | CV = 4% |
| lipase assay | 5 ± 2 | CV = 40% | 13 ± 4 | CV = 31% | 42 ± 6 | CV = 14% | 73 ± 7 | CV = 10% | 97 ± 4 | CV = 4% |
| total proteins assay by fluorescence spectroscopy | 5 ± 2 | CV = 40% | 13 ± 3 | CV = 23% | 45 ± 6 | CV = 13% | 74 ± 5 | CV = 7% | 96 ± 2 | CV = 2% |

Figure 4A:
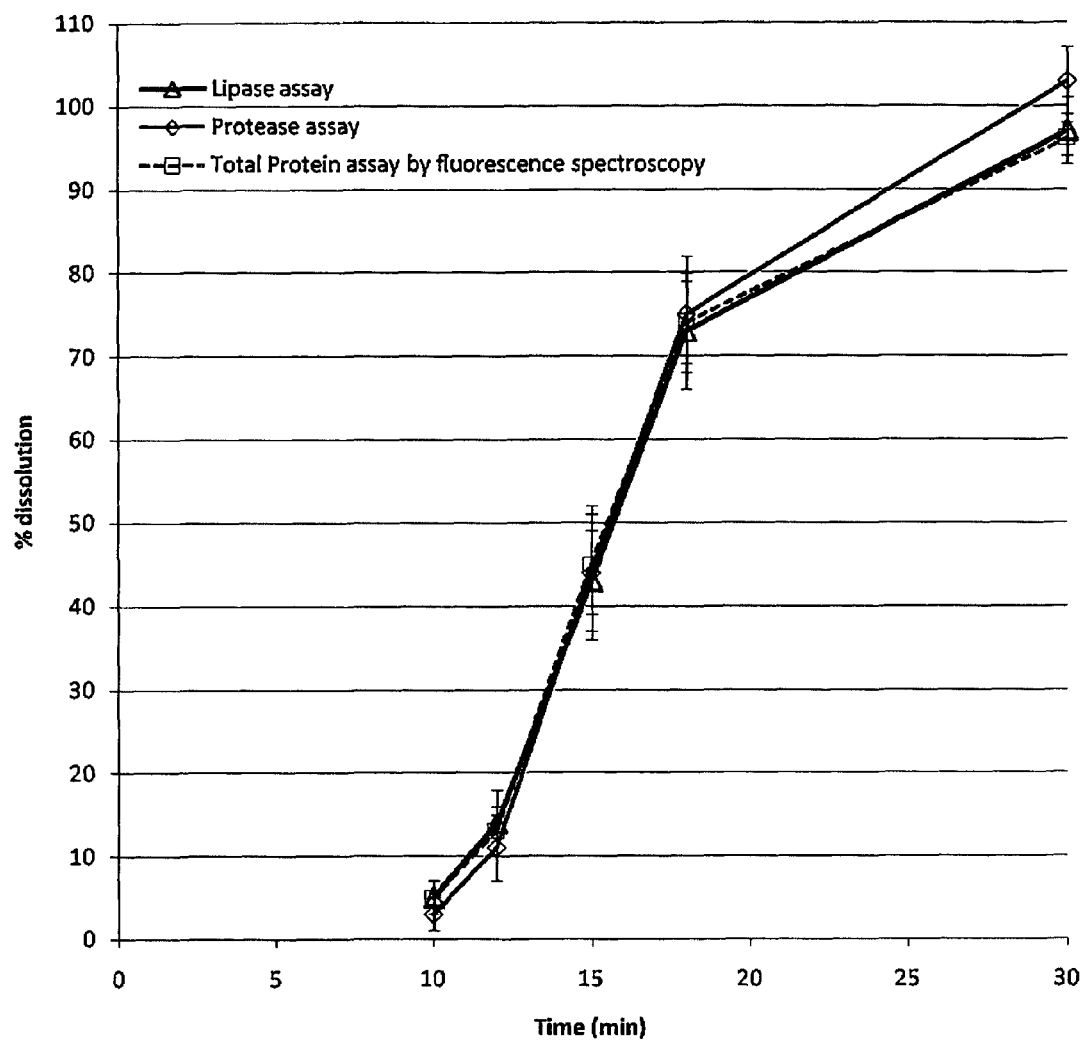
FIG. 4a. Dissolution profiles of pancrelipase beads (Zenpep® minitablets): enzyme-specific measurements vs fluorometric determination of total proteins content.
Figure 4B:
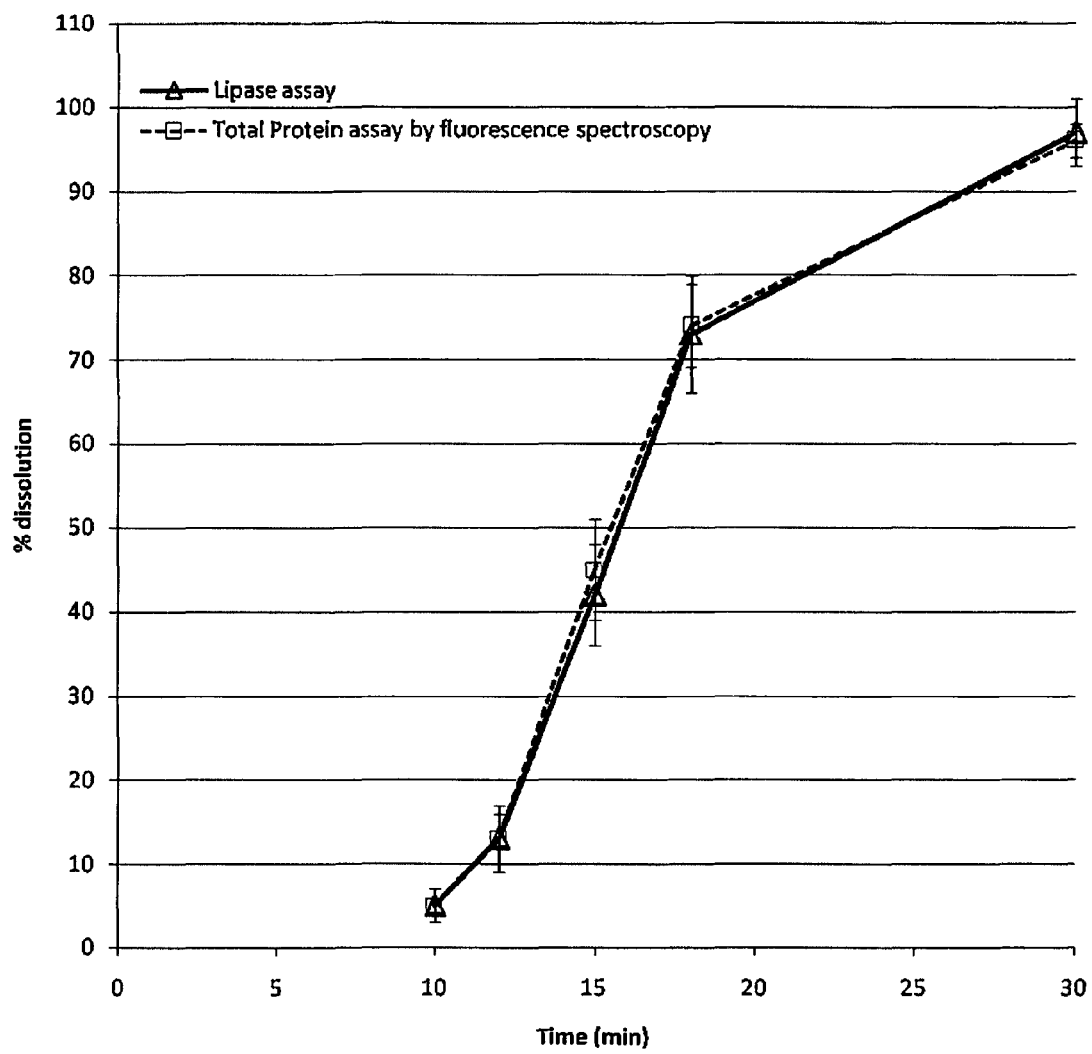
FIG. 4b. Dissolution profiles of pancrelipase beads (Zenpep® minitablets): lipase assay vs fluorometric determination of total proteins content.
Figure 4C:
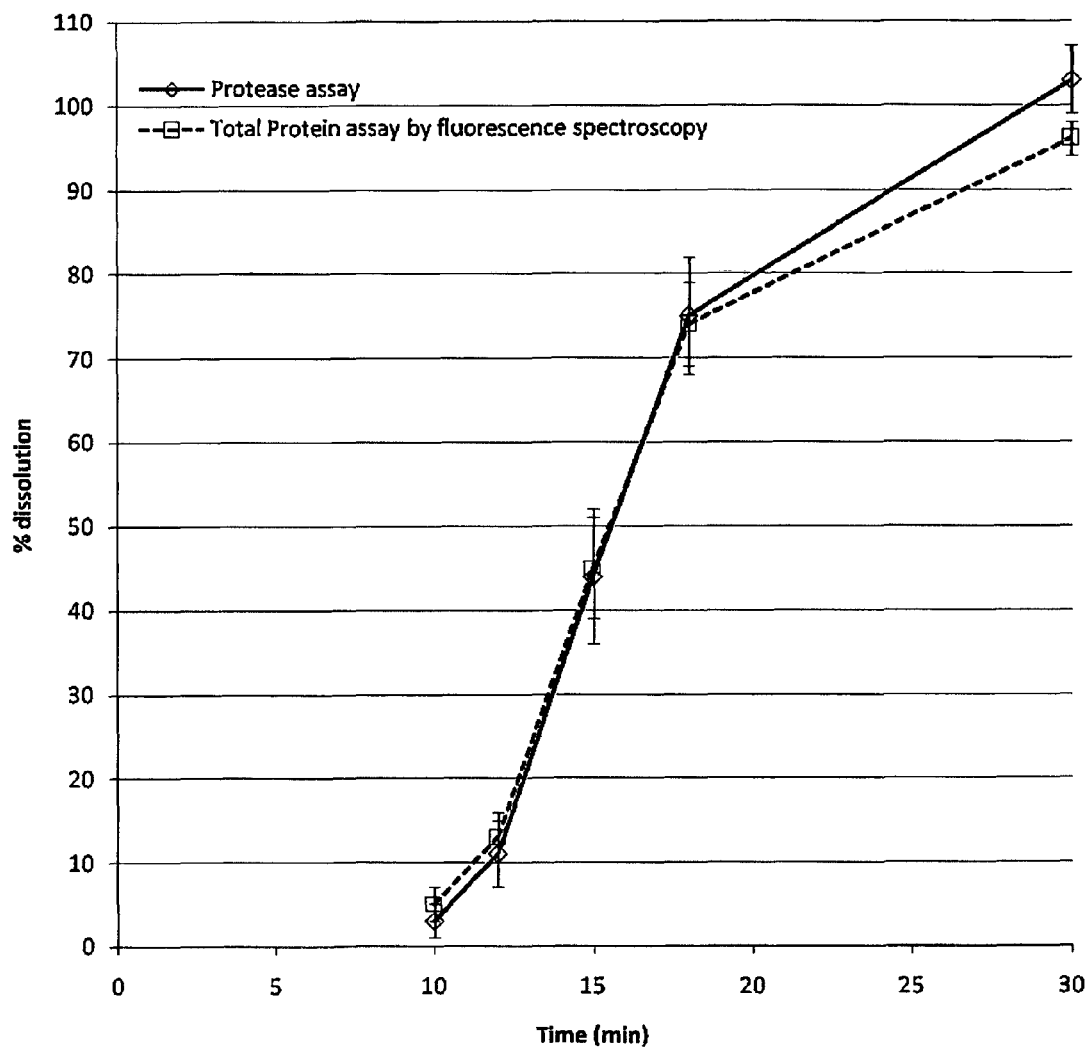
FIG. 4c. Dissolution profiles of pancrelipase beads (Zenpep® minitablets): protease assay vs fluorometric determination of total proteins content.

The three dissolution profiles show a nearly complete overlapping, as illustrated in the graphical comparison of FIGS. 4a-c; in particular, lipase assay and fluorimetric assay mean curves are completely superimposable, while protease mean curve only differs at the endpoint showing a value >100%. Also the CVs of each series of data is quite similar among the three measurement methods, with the lower values exhibited by the fluorometric assay.

The SUPAC approach used to evaluate the equivalence of the performance of a drug product after and before changes (similarity test f2 on the dissolution profiles of the products to compare) is used to show the equivalence of the new proposed method for the fluorometric determination of total proteins in the dissolution test of Zenpep® formulation with the one currently used (lipase assay) and with the other enzyme-specific measurement (protease assay).

To apply the similarity test f2 on the dissolution profiles, the FDA guidelines (Guidance for Industry "SUPAC MR: Modified release solid oral dosage forms. Scale-up and postapproval changes: chemistry, manufacturing, and controls, in vitro dissolution testing, and in vivo bioequivalence documentation" Center for Drug Evaluation and Research (CDER), September 1997; Guidance for Industry—dissolution testing of Immediate Release Solid Oral Dosage Forms, Center for Drug Evaluation and Research (CDER), August 1997) indicate some conditions that should be fulfilled:
 a. use the mean dissolution values (n=12) from both curves at each time interval,
 b. only one measurement should be considered beyond 85% dissolution point,
 c. the average difference at any sampling time point should not be greater than 15% between the dissolution profiles,
 d. to allow use of mean data, the percent coefficient of variation at the earlier time point should not be more than 20%, and at other time points should not be more than 10%.

The requirements a, b and c are fulfilled in the present dissolution data; however, CV values greater than those allowed (d) were observed at the first three timepoints (10, 12, 15 min) for all the measurement methods evaluated. The observed high variability of these timepoints can be explained with the very low concentration of the analyte at the first sampling time (10 min) and with the intrinsic variability of the formulation in the narrow range of elapsed time for the further timepoints at 12 and 15 minutes, taking into account that the 100% release of the formulation is obtained in a very short time (30 minutes) in the dissolution test conditions.

Based on the above consideration, the f2 test is applied anyway, assuming that the observed similar variability in the three measurement methods did not alter significantly the average curves obtained, showing full overlap. A further evaluation is then made by taking into account the last three timepoints (15-18-30 min), in order to verify if the f2 test would pass even with the data which fulfill completely the SUPAC requirements.

Example 5.4.1

Comparison: Fluorimetric Determination Content Vs Lipase Assay

The f2 test for the dissolution profiles of fluorimetric determination vs lipase assay (reference), showed a similarity of 87.4% between the two curves when all the timepoints are considered, while the similarity was 83.3% when the calculation is made on the last three timepoints.

Example 5.4.2

Comparison: Fluorimetric Determination of Total Proteins Content Vs Protease Assay The f2 test for the dissolution profiles of fluorimetric determination vs protease assay (reference), showed a similarity of 72.3% between the two curves when all the timepoints were considered, while the similarity was 68.6% when the calculation was made on the last three timepoints. Generally, f2 values greater than 50 (50-100) ensure sameness or equivalence of the two curves and, thus, of the performance of the test. According to the results obtained in the comparison of dissolution profiles by means of f2 test is therefore possible to state that the fluorometric determination of total proteins content is, in all respects, equivalent to the enzyme-specific methods in the measurement of API release in dissolution test of pancrelipase formulations (Zenpep® formulations).

Example 6

Comparison of Validation Data

To complete the comparison between the new fluorimetric test and the known accepted lipase activity enzymatic assay (USP method), Table 7 is included.

TABLE 7

Comparison of Validation Data

| | lipase assay | fluorimetric method |
|---|---|---|
| Specificity (towards formulation excipients) | % recovery of DS + excipient mix on the theor. DS assay = 101.8-103.5% | % interference in the FL reading (excipients/DS) = 1.6% |
| Range | 9.6-14.4 USP lipase units/mL (a) | 0.03-0.65Lipase units/mL (0.3-6.7 µg DS/mL) (b) |
| Linearity | y = 0.0123 + 0.0075x<br>$R^2$ = 0.9969 | y = 5.52 + 68.75x<br>$R^2$ = 0.9992 |
| Accuracy | 102.4% (level 80% of target conc)<br>101.0% (level 100% of target conc.)<br>97.6% (level 120% of target conc.) | 107.8% (level 10% of target conc.)<br>104.8% (level 100% of target conc.)<br>104.5% (level 200% of target conc.) |
| Precision | Repeatability CV = 1.6% (c)<br>Intermediate CV = 1.6% (c) | Repeatability CV = 1.1-2.0% (d)<br>Intermediate CV = 1.0-1.9% (d) |
| Stability of the marker in the enteric stage medium at 37° C. | After 30 minutes: 88-90% of the initial lipase assay | After 30 minutes: 97% of the initial FL reading |

(a): target concentration for lipase assay = 12 lipase units/mL;
(b): target concentration for FL assay = 0.3 lipase units/mL (3 µg DS/mL);
(c): 1 lot of DP, six independent samples/run;
(d): 6 lots of DP, six independent samples/run for each lot

Example 7

Dissolution Test by Fluorimetric Spectroscopy on Pancrelipase Beads

The fluorimetric method as described in the above examples is carried out also with other pancrelipase formulations present on the market with the name Creon® having different dosage strengths. The results are compared with those obtained for pancrelipase beads marketed as Zenpep® and are reported in FIG. 5. The differences in the behavior are in agreement with the different strengths of the formulations and the different surface areas of the particles of the two formulations (Zenpep®, Creon®). Two beads sizes are used for different Zenpep® strengths, the smaller ones (about 1.8 mm average diameter), showing faster dissolution profiles, are used to fill 5,000 UI capsules, while the bigger ones (about 2.4 average diameter) are used to fill 20,000 UI capsules. Creon® beads are about 1 mm average diameter, but significantly more irregular than Zenpep®s beads, thus providing faster dissolution profiles than Zenpep®, but less reproducible from batch to batch (all Creon® strengths use the same granules).

Example 8

Dissolution Test Combined with Gastro-Resistance Test: FL-Test Plus GR-Test FL-Test: Dissolution Test with Fluorimetric Measurement 800 mL of the acid stage medium are placed in each vessel of the dissolution bath equipped with basket apparatus (USP Apparatus 1—basket); the dissolution medium is (acid stage) equilibrated at 37° C. An amount of pancrelipase beads corresponding to 11,200 USP lipase units (10 capsules of Zenpep® minitabs or microtabs) is weighed and transferred into each basket of Apparatus 1. The apparatus is operated at 100 rpm. After 1 hour the baskets are removed from the medium, rinsed with a few milliliters of water and the content of each basket is transferred into the dissolution vessels containing 800 mL of the enteric stage medium at 37° C. of the dissolution bath equipped with paddle apparatus (USP Apparatus 2). The apparatus is operated at 100 rpm. After 30 min a 10-mL portion of the solution under test is removed, transferred to a test tube and equilibrated at r.t. A further dilution with enteric stage medium is made to obtain the proper concentration (about 0.3 USP units/mL). The solutions are stored in ice/water bath and manually shaken before reading. The diluted solutions are read in the fluorescence spectrometer with the following operative parameters: 1-cm pathlength quartz cuvette; excitation wavelength:=280 nm; emission wavelength (measurement)=346 nm; Excitation slit:=6.0.

The target concentration of the marker (API=pancrelipase; 100% released) in the diluted test solution is 0.3 USP lipase units/mL.

The standard solution is prepared as described in Example 1 and is stored in ice/water bath under stirring until reading.

The amount of release of the drug from the pancrelipase solid composition is calculated as follows.

Calculations are carried out for bulk minitabs/microtabs.

$$\% \text{ dissolution} = \frac{LC \times PS \times VC}{LS \times PC \times VS} \times 100$$

Calculations are carried out for capsules.

$$\% \text{ dissolution} = \frac{LC \times PS \times VC}{LS \times PC \times VS} \times \frac{US \times PM}{UL} \times 100$$

Wherein: LC is fluorescence reading (emission at 346 nm) of the sample; LS: fluorescence reading (emission at 346 nm) of the standard; PS is standard weight (mg); PC is sample weight (mg); US is potency of the standard (lipase USP units/mg, batch lipase assay); PM is mean weight of the capsule content (mg/capsule); UL is labeled content of lipase in the individual dosage unit (USP units/capsule); VC is dilution volume of the sample (mL); VS is dilution volume of the standard (mL).

GR Test: Gastroresistance Test (with Lipase Assay)

800 mL of the acid medium are placed in each vessel (USP Apparatus 1—Basket) of the dissolution bath equipped with basket apparatus and then the dissolution medium is equilibrated at 37° C. An amount of pancrelipase beads corresponding to 11,200 USP lipase units (10 capsules of Zenpep® minitabs or microtabs) is weighed and transferred into each basket of Apparatus 1. The apparatus is operated at 100 rpm. After 1 hour the baskets are removed from the medium and the samples are rinsed by dipping briefly (for about 5 seconds) the baskets in a 1,000 mL beaker containing 900 mL of cold purified water at 4° C., and this process is repeated three times, without changing the rinsing medium. The content of each basket is quantitatively transferred to a ceramic mortar, add 5-6 mL of cold purified water. The sample is ground until a complete dispersion of it is obtained, quantitatively collected into a 200 mL volumetric flask and the mortar well is rinsed. This operation is repeated 2-3 times. Purified water is added to final total volume. A further dilution with cold purified water to obtain the proper concentration (about 14 USP units/mL, which is theoretical max concentration available assuming 100% gastroresistance of the product) is done. The sample solution is prepared immediately before the titration and is kept under stirring in an ice/water bath.

The standard solution is prepared as follows: an amount of USP Pancreatin lipase RS, or pancrelipase working standard, corresponding to 6,000 USP Units is accurately weighted and added into a ceramic mortar, about 5-6 mL of purified water are added and followed by grinding. The liquid from the mortar is poured into a 500-mL volumetric flask and the mortar is also rinsed. This operation is repeated 2-3 times. Purified water is added to total final volume. The standard solution is prepared immediately before the titration and is kept under stirring in an ice/water bath.

The final concentration of the standard solution is about 12.0 USP Units lipase/mL.

For the lipase assay: 30 mL of the substrate emulsion (at 37°±0.1° C.) are poured in the jacketed vessel of the titrator, and stirred by a magnetic stirrer, maintaining the temperature at 37°±0.1° C. 0.1 N NaOH is added to adjust the pH to 9.20-9.23 potentiometrically. 1.0 mL of the sample or standard solution are added and followed by addition of 0.1N NaOH for 5 minutes to maintain the pH at 9.0.

The calculations are done with the following formula:

$$\% \text{ Gastroresistance} = \frac{VMC \times DC}{AVMS \times DS} \times \frac{PS \times US}{PC \times UC} \times 100$$

where: VMC is volume of 0.1N NaOH consumed per min by the sample (mL/min); AVMS is average volume of 0.1 N NaOH consumed per min by the standard (mL/min); PC is sample weight (mg), PS is weight of the standard (mg); DC is dilution of the sample (mL); DS is dilution of standard (mL); US is potency of the standard (lipase USP Units/mg); UC is batch lipase assay (USP lipase units/mg).

The acceptance criteria according to USP, <711> dissolution—Delayed Release forms (acid stage), Acceptance Table 3 are:

Level 1 acceptance criteria: GR % shall be greater or equal to 90% for each individual unit;
Level 2 acceptance criteria: the average value of the GR of the 12 units (6 units in level 1, 6 units in level 2) is not less than 90% and no individual unit is lower than 75%;
Level 3 acceptance criteria: the average value of the GR of the 24 units (6 units in level 1, 6 units in level 2, 12 units in level 3) is not less than 90%, and no individual units is lower than 75%.

Based on all the above reported data and considerations, the fluorometric measurement of total proteins content as marker of the digestive enzymes released in dissolution testing of pancrelipase beads is a reliable and advantageous alternative to the current accepted compendia measurement method based on the assay of lipase activity.

We claim:

1. A process for measuring an amount of digestive enzymes released from a solid pancrelipase composition in a dissolution medium using fluorescence spectroscopy for measuring the amount of digestive enzymes released from the composition in the dissolution medium, the process comprising the steps of: (a) allowing the solid pancrelipase composition to release the digestive enzymes in the dissolution medium, and (b) reading the fluorescence to measure the amount of digestive enzymes in the medium,
wherein the dissolution medium includes at least two media that are applied sequentially,
wherein the step (a) further comprises adding the solid pancrelipase composition in a first dissolution medium to form a suspension, transferring the suspension in a second dissolution medium, and allowing the release of the digestive enzymes, and the step (b) further comprises sampling aliquots of dissolution medium, reading fluorescence at 346 nm, and calculating the amount of digestive enzymes released.

2. The process of claim 1, wherein the solid pancrelipase composition is an enteric coated pancrelipase composition.

3. The process of claim 1, wherein the dissolution medium includes at least two media selected from the group consisting of water, HC1 solution, simulated gastric fluid, buffer solution, simulated intestinal fluid, aqueous and buffer solution containing at least one surfactant.

4. The process of claim 1, wherein the first dissolution medium is an aqueous medium having pH between about 1 and about 4.5 and the second dissolution medium is aqueous buffer solution having pH above about 5.

5. The process of claim 1, wherein the first dissolution medium is an aqueous medium having pH between about 1 and about 2.

6. The process of claim 1, wherein the second dissolution medium is aqueous buffer solution having pH between about 5.5 and about 6.8.

7. The process of claim 1, wherein the first dissolution medium is an aqueous medium having pH of about 1.2 and the second dissolution medium is aqueous buffer solution having pH of about 6.

8. The process of claim 1, wherein the solid pancrelipase composition has a total of about 750, about 3,000, about 4,200, about 5,000, about 6,000, about 10,000, about 10,500, about 15,000, about 16,800, about 20,000, about 21,000, about 24,000, or about 25,000, or about 40,000 USP lipase units or multiple thereof; or about 5,000, or about 10,000, or about 15,000 or about 20,000 or about 30,000, or about 40,000 PhEur lipase units or multiple thereof.

9. The process of claim 1 combined with a gastroresistance test, wherein a residual lipase activity of the composition in aqueous medium having pH between about 1 and about 4.5 is measured by an enzymatic lipase assay method.

10. The process of claim 9 combined with a gastroresistance test, wherein a residual lipase activity of the composition in aqueous medium having pH between about 1 and about 2 is measured by the enzymatic lipase assay method.

11. The process of claim 9 combined with a gastroresistance test, wherein a residual lipase activity of the composition in aqueous medium having pH of about 1.2 is measured by the enzymatic lipase assay method.

12. The process of claim 9 wherein the measuring of the amount of digestive enzymes released from the solid composition in dissolution medium by fluorescence spectroscopy is carried out either before or after the gastroresistance test.

13. The process of claim 12, wherein the measuring of the amount of digestive enzymes released from the solid composition in dissolution medium by fluorescence spectroscopy is carried in dissolution medium that consists of at least two media that are used sequentially.

14. The process of claim 13, wherein the first dissolution medium is an aqueous medium having acid pH between about 1 and about 4.5.

15. The process of claim 13, wherein the first dissolution medium is an aqueous medium having pH between about 1 and about 2.

16. The process of claim 13, wherein the second dissolution medium is aqueous buffer solution having pH above about 5.

17. The process of claim 13, wherein the second dissolution medium is aqueous solution having pH between about 5.5 and about 6.8.

18. The process of claim 13, wherein the first dissolution medium is an aqueous medium having pH of about 1.2 and the second dissolution medium is aqueous buffer solution having pH of about 6.

19. The process of claim 9 wherein the pancrelipase compositions have a total of about 750, about 3,000, about 4,200, about 5,000, about 6,000, about 10,000, about 10,500, about 15,000, about 16,800, about 20,000, about 21,000, about 24,000, about 25,000, or about 40,000 USP lipase units or multiple thereof; or about 5,000, or about 10,000, or about 15,000 or about 20,000 or about 30,000, or about 40,000 PhEur lipase units or multiple thereof.

20. The process of claim 12, wherein the measuring of the amount of digestive enzymes released from the solid composition in dissolution medium by gastroresistance test is carried in aqueous medium having acid pH between about 1 and about 4.5.

* * * * *